US009809798B2

(12) United States Patent
Raghunath et al.

(10) Patent No.: US 9,809,798 B2
(45) Date of Patent: Nov. 7, 2017

(54) PERICYTE PROGENITORS FROM PERIPHERAL BLOOD

(75) Inventors: Michael Raghunath, Singapore (SG); Anna Blocki, Singapore (SG)

(73) Assignee: National University of Singapore, Singapore (SG)

( * ) Notice: Subject to any disclaimer, the term of this patent is extended or adjusted under 35 U.S.C. 154(b) by 278 days.

(21) Appl. No.: 14/004,349

(22) PCT Filed: Mar. 12, 2012

(86) PCT No.: PCT/SG2012/000083
§ 371 (c)(1),
(2), (4) Date: Sep. 10, 2013

(87) PCT Pub. No.: WO2012/125123
PCT Pub. Date: Sep. 20, 2012

(65) Prior Publication Data
US 2014/0004046 A1   Jan. 2, 2014

Related U.S. Application Data

(60) Provisional application No. 61/451,637, filed on Mar. 11, 2011.

(51) Int. Cl.
*C12N 5/071* (2010.01)
*A61K 38/00* (2006.01)

(52) U.S. Cl.
CPC ........... *C12N 5/069* (2013.01); *C12N 5/0692* (2013.01); *A61K 38/00* (2013.01); *C12N 2500/38* (2013.01); *C12N 2502/28* (2013.01); *C12N 2533/52* (2013.01); *C12N 2533/70* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 4,582,802 A | 4/1986 | Zimmerman et al. | |
| 5,523,286 A | 6/1996 | McGlave et al. | |
| 5,665,572 A | 9/1997 | Ikeda et al. | |
| 5,804,446 A | 9/1998 | Cerami et al. | |
| 5,972,603 A | 10/1999 | Bedford et al. | |
| 6,114,150 A | 9/2000 | Weissman et al. | |
| 6,248,857 B1 | 6/2001 | Misumi et al. | |
| 6,300,073 B1 | 10/2001 | Zhao et al. | |
| 6,428,986 B1 | 8/2002 | Lapidot et al. | |
| 6,656,685 B2 | 12/2003 | Utermohlen et al. | |
| 6,787,305 B1 | 9/2004 | Li et al. | |
| 7,138,275 B2 | 11/2006 | Kremer et al. | |
| 8,568,982 B2 | 10/2013 | Raghunath et al. | |
| 2003/0135030 A1 | 7/2003 | Guttman et al. | |
| 2004/0241713 A1 | 12/2004 | Mirzabekov et al. | |
| 2005/0112631 A1 | 5/2005 | Piepenburg et al. | |
| 2006/0171928 A1 | 8/2006 | Kuwana et al. | |
| 2008/0220466 A1 * | 9/2008 | Fulga ................... C12N 5/0634 435/34 |
| 2010/0124569 A1 | 5/2010 | Abbot et al. | |
| 2010/0150885 A1 | 6/2010 | Tseng et al. | |
| 2010/0279283 A1 | 11/2010 | Raghunath et al. | |
| 2011/0076770 A1 | 3/2011 | Sakai et al. | |
| 2011/0117066 A1 | 5/2011 | Ailhaud et al. | |
| 2011/0144009 A1 | 6/2011 | Boss et al. | |
| 2011/0207175 A1 | 8/2011 | El-Sabban et al. | |
| 2012/0322152 A1 | 12/2012 | Raghunath et al. | |
| 2014/0004046 A1 | 1/2014 | Raghunath et al. | |

FOREIGN PATENT DOCUMENTS

| | | | | |
|---|---|---|---|---|
| CN | 1181195 C | * | 12/2004 | |
| EP | 2418272 A1 | | 2/2012 | |
| JP | 1860196 A1 | * | 11/2007 | ........... C12N 5/0692 |
| WO | WO 94/18333 A1 | | 9/1994 | |
| WO | WO 00/44882 A2 | | 8/2000 | |
| WO | WO 01/92501 A1 | | 12/2001 | |
| WO | WO 03/053647 A2 | | 7/2003 | |
| WO | WO 2005/107772 A1 | | 11/2005 | |
| WO | WO 2006/012404 A2 | | 2/2006 | |
| WO | WO2006012404 A2 | * | 2/2006 | |
| WO | WO 2007/102162 A2 | | 9/2007 | |
| WO | WO 2007/149926 | | 12/2007 | |
| WO | WO 2008/018839 A1 | | 2/2008 | |
| WO | WO 2008/104064 A1 | | 9/2008 | |
| WO | WO 2009/156151 A1 | | 12/2009 | |
| WO | WO 2011/021194 A2 | | 2/2011 | |
| WO | WO2011021194 A2 | * | 2/2011 | |

(Continued)

OTHER PUBLICATIONS

Blocki, Anna, and Michael Raghunath. "Generating Multipotent Fibrocytes from Peripheral Blood under Macromolecular Crowding." Tissue Engineering and Regenerative Medicine International Society, EU Meeting 2010.*
Blocki, A., K. Bhakoo, and M. Raghunath. "A Novel Approach to Derive Pericyte Progenitors From Peripheral Blood." Tissue Engineering and Regenerative Medicine International Society Asia Pacific Meeting 2011.*
Quan, Timothy E., and Richard Bucala. "Culture and analysis of circulating fibrocytes." Arthritis Research: Methods and Protocols vol. 1 (2007): 423-434.*
Pilling, Darrell, and Richard H. Gomer. "Regulatory pathways for fibrocyte differentiation." Fibrocytes: New insights into tissue repair and systemic fibroses (2007): 37-60.*
Pilling, Darrell, Varsha Vakil, and Richard H. Gomer. "Improved serum-free culture conditions for the differentiation of human and murine fibrocytes." Journal of immunological methods 351.1 (2009): 62-70.*
Pilling, Darrell, et al. "Identification of markers that distinguish monocyte-derived fibrocytes from monocytes, macrophages, and fibroblasts." PloS one 4.10 (2009): e7475.*
Annes, J.P., et al., "Making Sense Of Latent TGFβ Activation", J Cell Sci, 116: 217-224 (2003).

(Continued)

*Primary Examiner* — Robert Yamasaki
(74) *Attorney, Agent, or Firm* — Hamilton, Brook, Smith & Reynolds, P.C.

(57) ABSTRACT

Thus, provided herein are pericyte progenitor cells (e.g., isolated pericyte progenitor cells), methods for generating pericyte progenitors in clinically relevant numbers for various applications applying macromolecular crowding during cell culture, and methods of using the pericyte progenitor cells.

21 Claims, 14 Drawing Sheets

(56) References Cited

FOREIGN PATENT DOCUMENTS

| WO | WO 2011/096893 A1 | 8/2011 |
|---|---|---|
| WO | WO 2011/108993 A1 | 9/2011 |
| WO | WO 2012/031015 A1 | 3/2012 |
| WO | WO 2012/125123 A1 | 9/2012 |
| WO | WO 2013/137826 A1 | 9/2013 |

OTHER PUBLICATIONS

Aumailley, M. and Gayraud, B., "Structure and Biological Activity of The Extracellular Matrix", J Mol Med, 76(3-4): 253-265 (1998).
Ayme-Southgate, A., et al., "Both Synchronous and Asynchronous Muscle Isoforms of Projectin (The Drospophila Bent Locus Product) Contain Functional Kinase Domains", The Journal of Cell Biology, 128: 393-403 (1995).
Ballantyne, K.N., et al., "Molecular Crowding Increases The Amplification Success of Multiple Displacement Amplification and Short Tandem Repeat Genotyping", Anal Biochem, 355(2): 298-303 (2006).
Bambara, R.A., "On The Processive Mechanism of *Escherichia coli* DNA Polymerast I", Journal of Biological Chemistry, 253(2): 413-423 (2008).
Banfi, A., et al., "Proliferation Kinetics and Differentiation Potential of Ex Vivo Expanded Human Bone Marrow Stromal Cells: Implications for Their Use in Cell Therapy", Exp Hematol, 28(6): 707-715 (2000).
Bellini, A. and Mattoli, S., "The Role of The Fibrocyte, A Bone Marrow-Derived Mesenchymal Progenitor, In Reactive and Reparative Fibroses", Laboratory Investigation, 87: 858-870 (2007).
Bissell, M.J. and Aggeler, J., "Dynamic Reciprocity: How Do Extracellular Matrix and Hormones Direct Gene Expression?", Prog Clin Biol Res, 249: 251-262 (1987).
Blow, N., "Cell Culture: Building A Better Matrix", Nature Methods, 6(8): 619-622 (2009).
Bogacka, I., et al., "Pioglitazone Induces Mitochondrial Biogenesis in Human Subcutaneous Adipose Tissue in Vivo", Diabetes, 54: 1392-1399 (2005).
Bonet, M.L., et al., "Pharmacological and Nutritional Agents Promoting Browning of White Adipose Tissue", Biochim Biophys Acta, 1831(5): 969-985 (2013).
Bongso, A., et al., "Isolation and Culture of Inner Cell Mass Cells From Human Blastocyts", Human Reproduction, 9(11): 2110-2117 (1994).
Borgel, J., et al., "Targets and Dynamics of Promoter DNA Methylation During Early Mouse Development", Nat Genet, 42(12): 1093-1100 (2010).
Boyd, A.C., "Turbo Cloning: A Fast, Efficient Method For Cloning PCR Products And Other Blunt-Ended DNA Fragments Into Plasmids", Nucleic Acids Research, 21(4): 817-821 (1993).
Bucala, R., et al. "Circulating Fibrocytes Define A New Leukocyte Subpopulation That Mediates Tissue Repair", Molecular Medicine, 1(1): 71-81 (1994).
Campagnolo, P., et al., "Human Adult Vena Saphena Contains Perivascular Progenitor Cells Endowed With Clonogenic and Proangiogenic Potential", Circulation, 121(15): 1735-1745 (2010).
Caron, J.M., "Induction of Albumin Gene Transcription in Hepatocytes by Extracellular Matrix Proteins", Molecular and Cellular Biology, 10(3): 1239-1243 (1990).
Cawthon, R.M., "Telomere Measurement by Quantitative PCR", Nucleic Acids Research, 30(10): e47-6 pages (2002).
Cedar, H., "DNA Methylation and Gene Activity", Cell, 53(1): 3-4 (1988).
Celi, F.S., "Brown Adipose Tissue—When It Pays To Be Inefficient", N Engl J Med, 360(15): 1553-1556 (2009).
Chamberlain, G., et al., "Concise Review: Mesenchymal Stem Cells: Their Phenotype, Differentiation Capacity, Immunological Features, and Potential for Homing", Stem Cells, 25: 2739-2749 (2007).
Charlton, L.M., et al., "Residue-Level Interrogation of Macromolecular Crowding Effects on Protein Stability", J. Am Chem Soc, 130: 6826-6830 (2008).
Chebotareva, N. A., et al., "Biochemical Effects of Molecular Crowding", Biochemistr (Moscow), 69(11): 1239-1251 (2004).
Chen, C., et al,. "Applying Macromolecular Crowding to Enhance Extracellular Matrix Deposition and its Remodeling in Vitro for Tissue Engineering and Cell-Based Therapies", Adv Drug Deliv Rev, 63(4-5): 277-290 (2011).
Chen, C.Z.C. and Raghunath, M., "Focus On Collagen: In Vitro Systems to Study Fobrogenesis and Antifibrosis—State of the Art", Fibrinogenesis & Tissue Repair, 2(7): 10 pages (2009).(2009).
Chen, C.Z.C., et al., "The Scar-In-A-Jar: Studying Potential Antiibfrotic Compounds From the Epigenetic To Extracelluar Level in a Singel Well", British Journal of Pharmacology, 158: 1196-1209 (2009).
Cheung, M.S., et al., "Molecular Crowding Enhances Native State Stability and Refolding Rates of Globular Proteins", PNAS, 102(13): 4753-4758 (2005).
Chomczynski, P. and Sacchi, N., "Single-Step Method Of RNA Isolation By Acid Guanidinium Thiocyanate-Phenol-Chloroform Extraction", Anal Biochem, 162: 156-159 (1987).
Chong, H., et al., "Immunocytochemical Localization Of Latent Transforming Growth Factor-β1 Activation by Stimulated Macrophages", Journal Of Cellular Physiology, 178(3): 275-283 (1999).
Corning, Surface Areas and Recommended Medium Volumes for Corning® Cell Culture Vessels, Application Note, 4 pages, (2012).
Corselli, M., et al., "Perivascular Ancestors Of Adult Multipotent Stem Cells", Arterioscler Thromb Vasc Biol, 30: 1104-1109 (2010).
Cortiella, J., et al., "Influence of Acellular Natural Lung Matrix on Murine Embryonic Stem Cell Differentiation and Tissue Formation", Tissue Eng Part A, 16(8): 2565-2580 (2010).
Crisan, M., et al., "A Perivascular Origin for Mesenchymal Stem Cells in Multiple Human Organs", Cell Stem Cell, 3:301-313 (2008).
Cypress, A.M. and Kahn, C.R., "Brown Fat as a Therapy for Obesity and Diabetes", Curr Opin Endocrinol Diabetes Obes, 17(2): 143-149 (2010).
Cypress, A.M., et al., "Identification and Importance of Brown Adipose Tissue in Adult Humans", NE J. Med, 360(15): 1509-1517 (2009).
Daley, W.P., et al., "Extracellular Matrix Dynamics in Development and Regenerative Medicine", Journal of Cell Science, 121: 255-264 (2008).
Deb-Rinker, P., et al., "Sequential DNA Methylation of the Nanog And Oct-4 Upstream Regions in Human NT2 Cells During Neuronal Differentiation", The Journal of Biological Chemistry, 280(8): 6257-6260 (2005).
DePalma, M., et al., "Tie2 Identifies a Hematopoietic Lineage of Proangiogenic Monocytes Required for Tumor Vessel Formation and a Mesenchymal Population of Pericyte Progenitors", Cancer Cell, 8(3): 211-26 (2005).
Dhar, K., et al., "Tumor Cell-Derived PDGF-B Potentiates Mouse Mesenchymal Stem Cells-Pericytes Transition and Recruitment Through an Interaction with NRP-1", Molecular Cancer, 9(209): 12 pages (2010).
DiGirolamo, C.M., et al., "Propagation and Senescence of Human Marrow Stromal Cells in Culture: A Simple Colony-Forming Assay Identifies Samples with the Greatest Potential to Propagate and Differentiate", British Journal of Haematology, 107: 275-281 (1999).
Ding, X.H., et al., "Histologic and Histogenetic Investigations of Intracranial Hemangioblastomas", Surgical Neurology, 67: 239-245 (2007).
DiPersio, C.M., et al., "The Extracellular Matrix Coordinately Modulates Liver Transcription Factors and Hepatocyte Morphology", Molecular and Cellular Biology, 11(9): 4405-4414 (1991).
Elbad, C., et al., "Human Multipotent Adipose-Derived Stem Cells Differentiate Into Functional Brown Adipocytes", Stem Cells, 27: 2753-2760 (2009).

(56) References Cited

OTHER PUBLICATIONS

Elbad, C., et al., "Oxtocin Controls Differentiation of Human Mesenchymal Stem Cells and Reverses Osteoporosis", Stem Cells, 26: 2399-2407 (2008).
Elcock, A.H., "Models of Macromolecular Crowding Effects and the Need for Quantitative comparison With Experiment", Curr Opin in Struc Biol, 20:196-206 (2010).
Ellis, R.J., "Macromolecular Crowding: An Important but Neglected Aspect of The Intracellular Environment", Curr Opin Struct Biol, 11(1): 114-119 (2001).
Ellis, R.J., "Macromolecular Crowding: Obvious but Unappreciated", Trends in Biochemical Sciences, 26(10): 597-604 (2001).
Extended European Search Report for European Application No. 12758340.9 "Pericyte Progenitors From Peripheral Blood", dated Aug. 15, 2014.
Flottmann, H. and Quadir, A., "Polyvinylpyrrolidone (PVP)—One of the Most Widely Used Excipients in Pharmaceuticals: An Overview", Drug Delivery Technology, 8(5): 22-27 (2008).
Fuchs, E., et al., "Socializing With the Neighbors: Stem Cells and Their Niche", Cell, 116: 769-778 (2004).
Fuchs, S., et al., "Retention of a Differentiated Endothelial Phenotype by Outgrowth Endothelial Cells Isolated From Human Peripheral Blood and Expanded in Long-Term Cultures", Cell Tissue Res, 326: 79-92 (2006).
Gaengel, K., et al., "Endothelial-Mural Cell Signaling in Vascular Development And Angiogenesis", Arterioscler Thromb Vase Biol, 29: 630-638 (2009).
GE Healthcare, Ficoll PM70, Ficoll PM400, Data File 18/1158-27-AB Cell Preparation, 6 pages, no date given.
Gesta, S., et al., "Developmental Origin of Fat: Tracking Obesity to Its Source", Cell, 131(2): 242-256 (2007).
Gottlieb, J., et al., "The Herpes Simplex Virus Type 1 UL42 Gene Product: A Subunit of DNA Polymerase That Functions to Increase Processivity", J of Virology, 64(12): 5976-5987 (1990).
Greenspan, P., et al., "Nile Red: A Selective Fluorescent Stain for Intracellular Lipid Droplets", The Journal of Cell Biology, 100: 965-973 (1985).
Gregoire, F.M., et al., "Understanding Adipocyte Differentiation", Physiological Reviews, 78(3): 783-809 (1998).
Griffin, M., et al., "Tranglutaminases: Nature's Biological Glues", Biochem J., 368: 377-396 (2002).
Grönniger, E., et al., "Aging and Chronic Sun Exposure Cause Distinct Epigenetic Changes in Human Skin", PLOS Genetics, 6(5): e1000971, 10 pages (2010).
Gronthos, S., et al., "Molecular and Cellular Characterisation of Highly Purified Stromal Stem Cells Derived From Human Bone Marrow", J Cell Science, 116: 1827-1835 (2003).
Guy, R.A., et al., "Real-Time PCR for Quantification of Giardia and Cryptosporidium in Environmental Water Samples and Sewage", Applied and Environmental Microbiology, 69(9): 5178-5185 (2003).
Hall, A.P., "Review of the Pericyte During Angiogenesis and its Role in Cancer and Diabetic Retinopathy", Toxicologic Pathology, 34: 763-775 (2006).
Harve, K.S., et al., "Macromolecular Crowding in Biological Systems: Dynamic Light Scattering (DLS) to Quantify the Excluded Volume Effect (EVE)", Biophysical Reviews and Letters,1(3):317-325 (2006).
Harve, K.S., et al., "Understanding How the Crowded Interior of Cells Stabilizes DNA/DNA and DNA/RNA Hybrids—in SilicoPredictions and in Vitro Evidence", Nucleic Acids Research, 38(1): 172-181 (2010).
Harve, K.S., et al., "Molecular crowding in vitro as means of emulating cellular interiors: When less might be more", PNAS, 105(51): E119.
Hughes, C.S., et al., "Matrigel: A Complex Protein Mixture Required For Optimal Growth of Cell Culture", Proteomics, 10(9): 1886-1890 (2010).

International Preliminary Report on Patentability for PCT/SG2011/000081, "Culture Additives to Boost Stem Cell Proliferation and Differentiation Response", date of mailing Sep. 13, 2012.
International Preliminary Report on Patentability for PCT/SG2012/000083, "Pericyte Progenitors From Peripheral Blood", date of mailing Sep. 17, 2013.
International Report on Patentability, corrected version, for PCT/SG2007/000248, "Method for Molecular Biology Applications", date of completion of report Nov. 3, 2008.
International Search Report and the Written Opinion of the International Searching Authority for PCT/SG2007/000248, "Method for Molecular Biology Applications", date of mailing Nov. 16, 2007.
Jaiswal, N., et al., "Osteogenic Differentiation of Purified , Culture-Expanded Human Mesenchymal Stem Cells in Vitro", J of Cellular Biochemisty, 64: 295-312 (1997).
Jansen, P.A.M., et al., "Expression of The Vanin Gene Family in Normal and Inflamed Human Skin: Induction by Proinflammatory Cytokines", J of Inves Dermatol, 129: 2167-2174 (2009).
Kadler, K.E., et al., "Collagen Fibrillogenesis: Fibronectin, Integrins, and Minor Collagens as Organizers and Nucleators", Current Opinion in Cell Biology, 20: 495-501 (2008).
Katare, R., et al., "Transplantation of Human Pericyte Progenitor Cells Improves the Repair of Infarcted Heart Through Activation of an Angiogenic Program Involving Micro-RNA-132", Circ. Res., 109(8): 894-906 (2011).
Klaassen, I., et al., "Molecular Basis of the inner Blood-Retinal Barrier snd Its Breakdown in Diabetic Macular Edema and Other Pathological Conditions", Progress in Retinal and Eye Research, 34: 19-48 (2013).
Kleinman, H.K., et al., "Isolation and Characterization of Type IV Procollagen , Laminin, and Heparan Sulfate Proteoglycan From the EHS Sarcoma", Biochemistry, 12(24): 6188-6193 (1982).
Klimanskaya, I., et al., "Human Embryonic Stem Cells Derived Without Feeder Cells", The Lancet, 365: 1636-1641 (2005).
Kotewicz, M.L., et al., "Cloning and Overexpression of Moloney Murine Leukemia Virus Reverse Transcriptase in *Esherichia coli*", Gene, 35(3): 249-258 (1985).
Kuwana, M., et al., "Human Circulating CD14+ Monocytes as a Source of Progenitors That Exhibit Mesenchymal Cell Differentiation", Journal of Leukocyte Biology, 74: 833-845 (2003).
Lamagna, C. And Bergers, G., "The Bone Marrow Constitutes a Resevoir of Pericyte Progenitors", Journal of Leukocyte Biology, 80: 677-681 (2006).
Lanctot, P.M., et al., "The Glycans of Stem Cells", Curr Opin Chem Biol, 11(4): 373-380 (2007).
Lareu, R.R., et al., "Collagen Matrix Deposition is Dramatically Enhanced in Vitro When Crowded With Charged Macromolecules: The Biological Relevance of the Excluded Volume Effect", FEBS Lett, 581(14): 2709-2714 (2007).
Lareu, R.R., et al., "Emulating a Crowded Intracellular Environment in Vitro Dramatically Improves RT-PCR Performance", Biochem Biophys Res Commun, 363: 171-177 (2007).
Lareu, R.R., et al., "In Vitro Enhancement of Collagen Matrix Formation and Crosslinking for Applications in Tissue Engineering: A Preliminary Study", Tissue Eng, 13(2): 385-391 (2007).
Lemischka, I.R. and Moore, K.A., "Interactive Niches", Nature, 425: 778-779 (2003).
Li, D., et al., "Effects of Dextran on Proliferation and Osteogenic Differentiation of Human Bone Marrow-Derived Mesenchymal Stromal Cells", Cytotherapy, 10(6): 587-596 (2008).
Li, J.J., and Tan, W., "Macromolecular Crowding Accelerates DNA Cleavage Reaction Catalyzed by DNA Nucleases", Polymer Preprints, American Chemical Society, Division of Polymer Chemistry, 43(1): 712-713 (2002).
Lilla, Jennifer, et al., "Metalloproteases and Adipogenesis: A Weighty Subject", American Journal of Pathology, 160(5): 1551-1554 (2002).
Liu, W. and Saint, D.A., "A New Quantitative Method of Real Time Reverse Transcription Polymerase Chain Reaction Assay Based on Simulation of Polymerase Chain Reaction Kinetics", Analytical Biochemistry, 302: 52-59 (2002).

(56) References Cited

OTHER PUBLICATIONS

Livak, K., "ABI Prism 7700 Sequence Detection System, User Bulliten 2". PE Applied Biosystems, Foster City, CA, 36 pages (1997).
Loe, F.C., et al., "Enhanced Adipogenic Differentiation of Mesenchymal Stem Cells (hMSCs) Through Application of the Excluded Volume Effect (EVE)", National University of Singapore presentation, 2007, poster.
Lu, K., et al., "Chapter 3. Bone Marrow-Derived Vascular Progenitors and Proangiogenic Monocytes in Tumors", Methods Enzymol, 445: 53-82 (2008).
Ludwig, T.E., et al., "Derivation of Human Embryonic Stem Cells in Defined Conditions", Nature Biotechnology, 24(2): 185-187 (2006).
Ma, Y.D., et al., "Differentiation of Mouse Embryonic Stem Cells in Blood", Current Protocols in Stem Cell Biology, Supplement 6: 1F.4.1-1F.4.19 (2008).
Mallon, B.S., et al., "Toward Xeno-Free Culture of Human Embryonic Stem Cells", Int J Biochem Cell Biol, 38(7): 1063-1075 (2006).
Martin, M.J., et al., "Human Embryonic Stem Cells Express an Immunogenic Nonhuman Sialic Acid", Nature Medicine, 11(2): 228-232 (2005).
Mauney, J. R., et al., "Matrix-Mediated Retention of Osteogenic Differentiation Potential by Human Adult Bone Marrow Stromal Cells During Ex Vivo Expansion", Biomaterials, 25(16): 3233-3243 (2004).
Melkoumian, Z., et al., "Synthetic Peptide-Acrylate Surfaces for Long-Term Self-Renewal and Cardiomyocyte Differentiation of Human Embryonic Stem Cells", Nature Biotechnology, 28(6): 606-610 (2010).
Meng, G., et al., "Extracellular Matrix Isolated From Foreskin Fibroblasts Supports Long-Term Xeno-Free Human Embryonic Stem Cell Culture", Stem Cells Development, 19(4): 547-556 (2010).
Minguell, J.J., et al. "Mesenchymal Stem Cells", Exp Biol Med, 226(6): 507-520 (2001).
Minton, A.P. and Wilf, J., "Effect of Macromolecular Crowding Upon the Structure and Function of an Enzyme: Glyceraldehyde-3-Phosphate Drhydrogenase", Biochemistry, 20(17): 4821-4826 (1981).
Minton, A.P., "Protein Folding: Thickening the Broth", Current Biology, 10(3): R97-R99 (2000).
Minton, A.P., "The Influence of Macromolecular Crowding and Macromolecular Confinement on Biochemical Reactions in Physiological Media", The Journal of Biological Chemistry, 276(14): 10577-10580 (2001).
Mosser, D.M. and Edwards, J.P., "Exprloring the Full Spectrum of Macrophage Activation", Nat Rev Immunol, 8(12): 958-969 (2008).
Motz, M., et al., "Elucidation of an Archaeal Replicaiton Protein Network to Generate Enhanced PCR Enzymes", The Journal of Biological Chemistry, 277(18): 16179-16188 (2002).
Nadalutti, C., et al., "Extracellular Transglutaminase 2 Has a Role in Cell Adhesion, Whereas Intracellular Transglutaminase 2 is Involved in Regulation of Endothelial Cell Proliferation and Apoptosis", Cell Proliferation, 44(1): 49-58 (2011).
Nashimoto, M., "Correct Folding of a Ribozyme Induces by Non-specific Macromoleules", Eur J Biochem, 267: 2738-2745 (2000).
Nedergaard, J., et al., "Unexpected Evidence for Active Brown Adipose Tissue in Adult Humans", Am J Physiol Endocrinol Metab, 293: E444-E452 (2007).
Neuhuber, B., et al., "Effects of Plating Density and Culture Time on Bone Marrow Stromal Cell Characteristics", Exp Hematol, 36(9): 1176-1185 (2008).
Notification Concerning Transmittal of Copy of International Preliminary Report on Patentability for International Application no. PCT/SG2013/000102 "Generation Of Brown Adipose Tissue (BAT) From Mesenchymal Cells" Date of mailing: Sep. 25, 2014.
Notification of Transmittal of the International Search Report and the Written Opinion of the International Searching Authority for PCT/SG2011/00081, "Culture Additives to Boost Stem Cell Proliferation and Differentiation Response", dated Jun. 19, 2011.
Notification of Transmittal of the International Search Report and the Written Opinion of the International Searching Authority for PCT/SG2012/000083, "Pericyte Progenitors From Peripheral Blood", dated Jun. 7, 2012.
Notification of Transmittal of the International Search Report and the Written Opinion of the International Searching Authority for PCT/SG2013/000102, "Generation of Brown Adipose Tissue (BAT) From Mesenchymal Cells", dated Jun. 13, 2013.
Ozerdem, U., et al., "Contribution of Bone Marrow-Derived Pericyte Precursor Cells to Corneal Vasculogenesis", Invest Ophthalmol Vis Sci, 46: 3502-3506 (2005).
Ozerdem, U., et al., "Early Contribution of Pericytes to Angiogenic Sprouting and Tube Formation", Angiogenesis, 6(3): 241-249 (2003).
Peng, Y. and Raghunath, M., "Learning From Nature: Emulating Macromolecular Crowding to Drive Extracellular Matrix Enhancement for the Creation of Connective Tissue in Vitro", in Tissue Engineering, Eber, D., ed., (Croatia: IN_TECH) Chapter 5.
Petrovic, N., et al. "Chronic Peroxisome Proliferator-Activated Receptor γ (PPARγ) Activation of Epididymally Derived White Adipocyte Cultures Reveals a Population of Themogenically Competent, UCP1-Containing Adipocytes Molecularly Distinct From Classic Brown Adipocytes", J of Biolo Chem, 285(10): 7153-7164 (2010).
Pittenger, M.F., et al., "Mulitilineage Potential of Adult Human Mesenchymal Stem Cells", Science, 284: 143-147 (1999).
Ponchel, F., et al., "Real-Time PCR Based on SYBR-Green I Fluorescence: An Alternative to the TaqMan Assay for a Relative Quantification of Gene Rearrangements, Gene Amplifications and Micro Gene Deletions", BMC Biotechnology, 3(18): 13 pages, (2003).
Raghunath, M., et al., "The Cutaneous Microfibrillar Aparatus Contains Latent Transforming Growth Factor-β Binding Protein-1 (LTBP-1) And is a Repository for Latent TGF-β1", J Invest Dermatol, 111: 559-564 (1998).
Rajantie, I., et al., "Adult Bone Marrow-Derived Cells Recruited During Angiogenesis Comprise Precursors for Periendothelial Vascular Mural Cells", Blood, 104(7): 2084-2086 (2004).
Rajkumar, V.S., et al., "Platelet Derived Growth Factor-β Receptor Activation is Essential for Fibroblast and Pericyte Recruitment During Cutandous Wound Healing", The American Journal of Pathology, 169(6): 2254-2265 (2006).
Rasmussen, R., et al., "Quantitative PCR by Continuous Fluorescence Monitoring of a Double Strand DNA Specific Binding Dye", Biochemica, 2: 8-11 (1998).
Ravussin, E. and Kozak, L.P., "Have We Entered the Brown Adipose Tissue Renaissance?", Obesity Reviews, 10:265-268 (2009).
Richards, M. and Bongso, A., "Propagation of Human Embryonic Stem Cells on Human Feeder Cells", Method Mol Biol, 331: 23-41 (2006).
Rifkin, D.B. and Moscatelli, D., "Recent Developments in the Cell Biology of Basic Fibroblast Growth Factor", J Cell Biol, 109: 1-6 (1989).
Rosen, E.D. and Spiegelman, B.M., "Molecular Regulation of Adipogenesis", Annu Rev Cell Dev Biol, 16: 145-171 (2000).
Rosso, F., et al., "From Cell-ECM Interactions to Tissue Engineering", J Cell Physio, 199: 174-180 (2004).
Rothwell, N.J. and Stock, M.J., "Luxuskonsumption, Diet-Induced Thermogenesis and Brown Fat: The Case in Favour", Clinical Science, 64: 19-23 (1983).
Saito, M., et al., "High Incidence of Metabolically Active Brown Adipose Tissue in Health Adult Humans: Effects of Cold Exposure And Adiposity", Diabetes, 58: 1526-1531 (2009).
Saksela, O., et al., "Endothelial Cell-Derived Heparan Sulfate Binds Basic Fibroblast Growth Factor and Protects it From Proteolytic Degradation", J Cell Biol, 107: 743-751 (1988).
Sasaki, Y., et al., "Effect of Molecular Crowding on DNA Polymerase Activity", Biotechnology J, 1(4): 440-446 (2006).
Schnell, S. and Mdonza, C., "Theoretical Description of the Polymerase Chain Reaction", J Theor Biol, 188(3): 313-318 (1997).

(56) References Cited

OTHER PUBLICATIONS

Schönherr, E. and Hausser H.J., "Extracellular Matrix and Cytokines: A Functional Unit", Developmental Immunology, 72(2-4): 89-101 (2000).
Scale, P., et al., "PRDM16 Controls a Brown Fat/Skeletal Muscle Switch", Nature, 454(7207): 961-967 (2008).
Seta, N. and Kuwana, M., "Human Circulating Monocytes as Multipotential Progenitors", Keio J Med, 56(2): 41-47 (2007).
Song, N., et al., "Overexpression of Platelet-Derived Growth Factor-BB Increases Tumor Pericyte Content Via Stromal-Derived Factor-1α/CXCR4 Axis", Cancer Res 69: 6057-6064 (2009).
Spiess, A.N. and Ivell, R., "A Highly Efficient Method for Long-chain cDNA Synthesis Using Trehalose and Betadine", Anal Biochem, 301(2): 168-174 (2002).
Spiess, A.N., et al., "Trehalose is a Potent PCR Enhancer: Lowering of DNA Melting Temperature and Thermal Stabilization of Taq Polymerase by the Disaccharide Trehalose", Clinical Chemistry, 50(7): 1256-1259.
Stenderup, K., et al., "Aging is Associated With Decreased Maximal Life Span and Accelerated Senescence of Bone Marrow Stromal Cells", Bone, 33(6): 919-926 (2003).
Supplementary European Search Report for EP 12758340, "Pericyte Progenitors From Peripheral Blood", date of mailing Aug. 25, 2014.
Taipale, J., et al., "Latent Transforming Growth Factor-β1 and its Binding Protein are Components of Extracellular Matrix Microfibrils", J Histochem Cytochem, 44: 875-889 (1996).
Tigges, U., et al., "FGF2-Dependent Meovascularization of Subcutaneous Matrigel Plugs is Initiated by Bone Marrow-Derived Pericytes and Macrophages", Development, 135: 523-532 (2008).
Tokuriki, N., et al., "Protein Folding by the Effects of Macromolecular Crowding", Protein Science, 13: 125-133 (2004).
Tondreau, T., et al., "Mesenchymal Stem Cells Derived From CD133-Positive Cells in Mobilized Peripheral Blood and Cord Blood: Proliferation, Oct4 Expression, and Plasticity", Stem Cells, 23: 1105-1112 (2005).
U.S. Department of Health and Human Services, National Institutes of Health, "The Adult Stem Cell", Stem Cell Information, 11 pages (2009).
Van der Maaren, J.R.C., "Introduction to Biopolymer Physics", *World Scientific*, 2007, 261 pages.
van Marken Lichtenbelt, W.D., et al., "Cold-Activated Brown Adipose Tissue In Healthy Men", NE J of Med, 360(15): 1500-1508 (2009).
Vernochet, C., et al., "C/EBPα and the Corepressors CtBP1 and CtBP2 Regulate Repression of Select Visceral White Adipose Genes During Induction of the Brown Phenotype in White Adipocytes by Peroxisome Proliferator-Activated Receptor γ Agonists", Mol and Cell Biol, 29(17): 4714-4728 (2009).
Villa-Diaz, L.G., et al., "Synthetic Polymer Coatings for Longterm Growth of Human Embryonic Stem Cells", Nature Biotechnolgy, 28(6): 581-583 (2010).
Virtanen, K.A., et al., "Functional Brown Adipose Tissue in Healthy Adults", NE J of Med, 360:1518-1525 (2009).
Wang, Z., et al., "Imprtance of Syndecan-4 and Syndecan-2 Osteoblast Cell Adhesion and Survival Mediated by a Tissue Transglutaminase-Fibronectin Complex", Experimental Cell Research, 317: 367-381 (2011).
Welter, J.F., et al., "Extracellular Matrix Decposition by Chondrogenically Differentiating Human Mesenchymal Stem Cells is Enhanced by Macromolecular Crowding", Osteoarthritis and Cartilage, 17(1) 494: S265 (2009).
Wenner, J.R. and Bloomfield, V.A., "Crowding Effects on EcoRV Kinetics and Binding", Biophysical Jouranl, 77: 3234-3241 (1999).
WHO Factsheet: Obesity and Overweight as downloaded on Jan. 30, 2014; URL: http://www.who.int/mediacentre/factsheets/fs311/en/index.html#(2011).
Witmer, A. N., et al., "In Vivo Angiogenic Phenotypes of Endothelial Cells and Pericytes Induced by Vascular Endothelial Growth Factor-A", Journal of Histochemistry & Cytochemistry, 52(1): 39-52 (2004).

Wray, J., et al., "The Ground State of Pluipotency", Biochem Soc Trans, 38: 1027-1032 (2010).
Xu, C., et al., "Feeder-Free Growth of Undifferentiated Human Embryonic Stem Cells", Nature Biotcchnolgy, 19: 971-974 (2001).
Yki-Järvinen, H., "Thiazolidinediones", NE J of Med, 351: 1106-1118 (2004).
Zhang, X-J, J., and Julin, D.A., "Isolation and Characterization of the C-Terminal Nuclease Domain From the RecB Protein of *Escherichia coli*", Nucleic Acids Research, 27(21): 4200-4207 (1999).
Zhao, Yong, et al., "A Human Peripheral Blood Monocyte-Derived Subset Acts as Pluripotent Stem Cells", PNAS, 100(5): 2426-2431 (2003).
Zhou, B.R., et al., "Mixed Macromolecular Crowding Accelerates the Oxidative Refolding of Reduced, Denatured Lysozyme", The Journal of Biological Chemistry, 273(53): 55109-55116 (2004).
Zimmerman, S.B. and Harrison, B., "Macromolecular Crowding Increases Binding of DNA Polymerase to DNA: An Adaptive Effect", PNAS, 84: 1871-1875 (1987).
Zingaretti, M.C., et al., "The Presence of UCP1 Demonstrates That Metabolically Active Adipose Tissue in the Neck of Adult Humans Truly Represents Brown Adipose Tissue", FASEB J, 23: 3113-3120 (2009).
Ang, S.M., et al., "Macromolecular Crowding Amplifies Adipogenesis of Human Bone Marrow-Derived Mesenchymal Stem Cells by Enhancing the Pro-Adipogenic Microenvironment", *Tissue Engineering, Part A*, 20(5 and 6):966-981 (2014).
Blocki, A., et al., "Sourcing of an Alternative Pericyte-Like Cell Type from Peripheral Blood in Clinically Relevant Numbers for Therapeutic Angiogenic Applications", *The American Society of Gene & Cell Therapy*, 23(3):510-522 (2015) plus 7 pages of Supplementary Information.
Deng, T., et al., "A Peroxisome Proliferator-Activated Receptor γ (PPARγ)/PPARγ Coactivator 1β Autoregulatory Loop in Adipocyte Mitochondrial Function", *The Journal of Biological Chemistry*, 286(35):30723-30732 (2011).
Huang, J., "PGC-1α Mediates Differentiation of Mesenchymal Stem Cells to Brown Adipose Cells", *Atherosclerosis and Thrombosis*, 18(11):966-980 (2011).
Kang, S., et al., "Effects of Wnt Signaling on Brown Adipocyte Differentiation and Metabolism Mediated by PGC-1α", *Molecular and Cellular Biology*, 25(4):1272-1282 (2005).
Lehr, L., et al., "Differentiation and Characterization in Primary Culture of White Adipose Tissue Brown Adipocyte-Like Cells", *International Journal of Obesity*, 33:680-686 (2009).
Loe, F.C., et al., "Macromolecular Crowding Improves the Microenvironment During Adipogenesis of Human Mesenchymal Stem Cells-Tool for Translation Tissue Engineering", 2nd TERMIS World Congress, in conjunction with the 2009 Seoul Stem Cell Symposium, held at the Lotte Hotel World, Seoul, S. Korea, Aug. 31-Sep. 3, 2009, Poster.
Morganstein, D.L., et al., "Human Fetal Mesenchymal Stem Cells Differentiate Into Brown and White Adipocytes: A Role for ERRα in Human UCP1 Expression", *Cell Research*, 20:434-444 (2010).
Nedergaard, J., et al., "PPARγ in the Control of Brown Adipocyte Differentiation", *Biochimica et Biophysica Acta*, 1740:293-304 (2005).
Pardo, R., et al., "Rosiglitazone-Induced Mitochondrial Biogenesis in White Adipose Tissue is Independent of Peroxisome Proliferator-Activated Receptor γ Coactivator-1α", *PLOSone*, 6(11):e26989, 13 pages (2011).
Richard, D. and Picard, F., "Brown Fat Biology and Thermogenesis", *Frontiers in Bioscience*, 16:1233-1260 (2011).
Schönfeld, P. and Wojtczak, L, "Brown Adipose Tissue Mitochondria Oxidizing Fatty Acids Generate High Levels of Reactive Oxygen Species Irrespective of the Uncoupling Protein-1 Activity State", *Biochimica et Biophysica Acta*, 1817:410-418 (2012).
Schultz, T.J., et al., "Identification of Inducible Brown Adipocyte Progenitors Residing in Skeletal Muscle and White Fat". PNAS, 108(1):143-148 (2011).
Tiraby, C., et al., "Acquirement of Brown Fat Cell Features by Human White Adipocytes", *The Journal of Biological Chemistry*, 278(35):33370-33376 (2003).

(56) References Cited

OTHER PUBLICATIONS

Tseng, Y-H., et al., "New Role of Bone Morphogenetic Protein 7 in Brown Adipogenesis and Energy Expenditure", *Nature*, 454:1000-1004 (2008).
Vetvicka, V. and Vetvickova, J., "β(1-3)-D-Glucan Affects Adipogenesis, Wound Healing and Inflammation", *Orient. Pharm Exp Med*, 11(3): 169-175 (2011).
Vila-Bedmar, R. and Fernandez-Veledo, S., "A New Era for Brown Adipose Tissue: New Insights into Brown Adipocyte Function and Differentiation", *Archives of Physiology and Biochemistry*, 117(3):195-208 (2011).
Zamani, N. and Brown, C.W., "Emerging Roles for the Transforming Growth Factor-β Superfamily in Regulating Adiposity and Energy Expenditure", *Enodcrine Review*, 32(3):387-403 (2011).
Zimmerman, S.B. and Trach, S.O., "Macromolecular Crowding Extends the Range of Conditions Under Which DNA Polymerase is Functional", *Biochimica et Biophysica Acta*, 949(3):297-304 (1988).
Zimmerman, S.B. and Minton, A.P., "Macromolecular Crowding: Biochemical, Biophysical and Physiological Consequences", *Annu Rev Biophys Biomol Struct*, 22: 27-65 (1993).
Supplementary European Search Report for EP 13761471, "Generation of Brown Adipose Tissue (BAT) From Mesenchymal Cells", date of mailing Oct. 26, 2015.
Final Office Action for U.S. Appl. No. 13/581,680 "Culture Additives to Boost Stem Cell Proliferation and Differentiation Response" dated Jun. 4, 2014.
Non-Final Office Action for U.S. Appl. No. 13/581,680 "Culture Additives to Boost Stem Cell Proliferation and Differentiation Response" dated Aug. 15, 2013.
Non-Final Office Action for U.S. Appl. No. 13/581,680 "Culture Additives to Boost Stem Cell Proliferation and Differentiation Response" dated Jan. 22, 2016.
Non-Final Office Action for U.S. Appl. No. 14/384,565 "Generation of Brown Adipose Tissue (BAT) From Mesenchymal Cells " dated May 12, 2016.
Notice of Allowance, U.S. Appl. No. 13/581,680, "Culture Additives to Boost Stem Cell Proliferation and Differentiation Response" dated Aug. 26, 2016.
Final Office Action for U.S. Appl. No. 14/384,565 "Generation of Brown Adipose Tissue (BAT) From Mesenchymal Cells" dated Aug. 29, 2016.
Löffler, G. and Hauner, H., "Adipose Tissue Development: The Role of Precursor Cells and Adipogenic Factors", Kline Wochenschrift, 65:812-817 (1987).
Marinello, F. and Tonti, G.A., "Concise Review: No Breakthroughs for Human Mesenchymal and Embryonic Stem Cell Culture: Conditioned Medium, Feeder Layer, or Feeder-Free; Medium with Fetal Calf Serum, Human Serum, or Entriched Plasma; Serum-Free, Serum Replacement Nonconditioned Medium, or Ad Hoc Formula? All That Glitters Is Not Gold", Stem Cells, 25(7):1603-1609 (2007).
Rashid, R., et al., "Macromolecular Crowding and Stem Cell Differentiation", 771-POS Board B571, Biophysical Journal, Feb. 9, 2011, 100(3) 142a-143a.
Stacey, D.H., et al., "In Vitro Adipogenic Differentiation of Preadipocytes Varies with Differentiation Stimulus, Culture Dimensionality, and Scaffold Composition", Tissue of Engineering, 15(11): 3389-3399 (2009).
Blocki, A., et al., "Generating Multipotent Fibrocytes from Peripheral Blood under Macromolecular Crowding", *Tissue Engineering and Regenerative Medicine International Society, eu Meeting* 2010.
Blocki, A., et al., "A Novel Approach to Derive Pericyte Progenitors From Peripheral Blood", *Tissue Engineering and Regenerative Medicine International Society Asia Pacific Meeting* 2011.

* cited by examiner

PERICYTE PROGENITORS FROM PERIPHERAL BLOOD

RELATED APPLICATION(S)

This application is the U.S. National Stage of International Application No. PCT/SG2012/000083, filed Mar. 12, 2012, which designates the U.S., published in English, and claims the benefit of U.S. Provisional Application No. 61/451,637, filed on Mar. 11, 2011. The entire teachings of the above applications are incorporated herein by reference.

BACKGROUND OF THE INVENTION

Pericytes are perivascular cells that are indispensable for normal blood vessel function by stabilizing maturing blood vessels, forming permeability barriers and regulating the blood flow. They also contribute to angiogenic sprouting and migrate to (re-) vascularising tissues and tumours from the bone marrow. While pericytes can be purified from tissue homogenates (e.g., placenta, muscle), their origin is still controversial and no other less-invasive or destructive method is known to generate them in vitro for therapeutic purposes.

Identification and isolation of a pericyte precursor would therefore be of great use in treatment of ischemic injuries like myocardial infarction, congestive heart failure, stroke, and peripheral vascular disorders.

SUMMARY OF THE INVENTION

The cell culture technique described herein uses the biophysical principle of macromolecular crowding (MMC). MMC has been used to enhance matrix deposition (Lareu et al 2007 Tissue Engineering, 13(2):385-391; Lareu et al. 2007 FEBS Lett 581(14):2709-2714) essentially changing microenvironments (Chen et al 2011). Thus, MMC not only amplifies the differentiation response of MSC's, but also boosts their proliferation in the undifferentiated stage by almost 10 fold without the use of growth factors (see WO 2011/108993 which is herein incorporated by reference). Shown herein is that cultivation of buffy coats (mononuclear cell fraction) from peripheral blood under MMC gives rise to pericyte progenitors. Pericytes are a peculiar cell type that originates from the bone marrow and are required for revascularising tissue after trauma and chronic damage and have homing capacity. Thus, pericyte progenitors are an attractive as alternative to bone marrow derived mesenchymal stem or progenitor cells for the treatment of acute or chronic ischemic situations like stroke, myocardial infarction, congestive heart failure and peripheral vascular disorders.

Accordingly, in one aspect, the invention is directed to isolated pericyte progenitor cells. Depending upon the time of isolation, the pericyte progenitors express only one or more markers described herein (some (e.g., two or more) of the markers; only some (e.g., two) of the markers). Thus, the isolated pericyte progenitor cells can comprise, consist essentially of, or consist of one or more of the markers described herein.

In another aspect, the invention is directed to a method of obtaining pericyte progenitor cells comprising culturing blood cells with a matrix to which cells can attach and one or more organic-based hydrophilic macromolecules, thereby producing a cell culture. The cell culture is maintained under conditions in which pericyte progenitor cells are generated (e.g., expanded, increased) in the cell culture, thereby obtaining pericyte progenitor cells.

In another aspect, the invention is directed to pericyte progenitor cells produced by the methods described herein. As will be appreciated by those of skill in the art, the pericyte progenitor cells can comprises a label that can be detected directly or indirectly (a detectable label) using a variety of techniques known to those of skill in the art.

In yet another aspect, the invention is directed to a pharmaceutical composition comprising the pericyte progenitor cells described herein. In a particular aspect, the pharmaceutical composition comprises detectably labeled pericyte progenitor cells.

In a particular aspect, the invention is directed to a method of enhancing growth of one or more blood vessels (angiogenesis) in an individual in need thereof comprising administering pericyte progenitor cells to the individual, thereby enhancing sprouting and survival of the one or more blood vessels in the individual. The pericyte progenitors can be administered systemically, wherein the pericyte progenitors will home or migrate to the site of blood vessel growth, and/or locally at the site of blood vessel growth in the individual.

In another aspect, the invention is directed to a method of detecting one or more sites of angiogenesis in an individual in need thereof comprising detecting pericyte progenitor cells in the individual, wherein one or more sites at which the pericyte progenitor cells is detected is an indication of angiogenesis at the one or more sites in the individual. In a particular aspect, the method can further comprise administering detectably labeled pericyte progenitor cells to the individual and detecting the detectably labeled progenitor pericytes in the individual. The detectably labeled pericyte progenitors will migrate to a site of angiogenesis that is occurring such as at a site of a tumor, a site of tissue regeneration, a site of ischemic injury, a site of a wound or a combination thereof in the individual.

In yet another aspect, the invention is directed to a method of homing an agent to a site (causing or directing an agent to migrate to a site) of angiogenesis in an individual in need thereof, comprising administering the agent to the individual wherein the agent is attached to one or more pericyte progenitor cells which home to a site of angiogenesis in the individual, thereby delivering the agent to the site of angiogenesis in the individual. In a particular aspect, the pericyte progenitor cells further comprise a detectable label. The pericyte progenitors migrate to a site of angiogenesis that is occurring at a site of a tumor, a site of tissue regeneration, a site of ischemic injury, a site of a wound or a combination thereof in the individual.

In another aspect, the invention is directed to a kit for obtaining pericyte progenitor cells from blood comprising a matrix to which blood cells can attach and one or more organic-based hydrophilic macromolecules and instructions for use thereof.

DETAILED DESCRIPTION OF THE INVENTION

Figure 1:
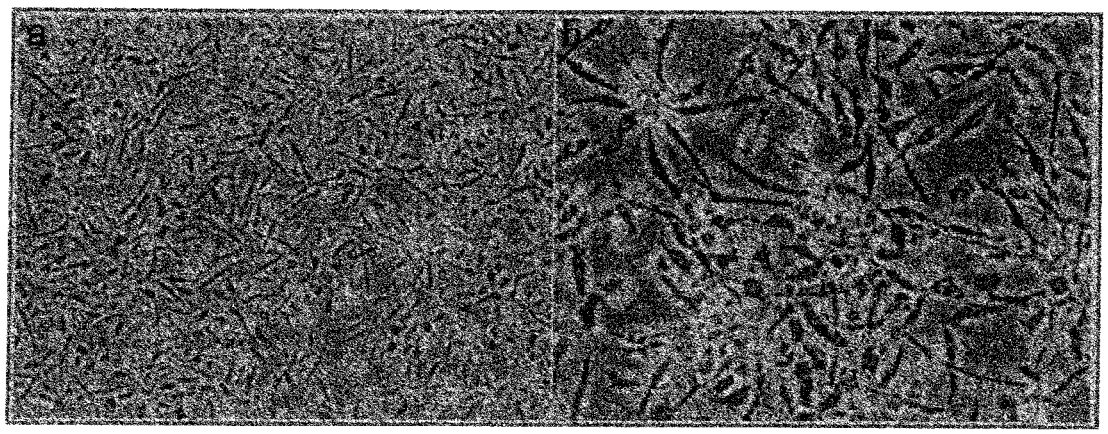
FIG. 1 shows phase contrast photographs at a) 10× magnification (scalebar: 200 µm) and b) 20× magnification (scalebar: 100 µm) of pericyte progenitor formation in culture.

Pericytes originate from bone marrow, but whether they can be assigned to the mesenchymal or haematopoietic lineage is currently a matter of debate. Dhar et al. (Dhar et al. 2006 Mol Cancer 5(9):209 showed that mouse embryonic MSC, when induced by tumor-cell derived conditioned medium, can be differentiated into cells expressing pericyte marker α-SMA and desmin and attach to formed vessels in vitro and in vivo. Furthermore, it was demonstrated that pericyte isolated from various human organs like skeletal muscle, pancreas, adipose tissue and placenta lack haematopoietic and mature endothelial cell markers, share markers with MSC in vitro and in vivo and can differentiate in various mesenchymal lineages like adipocytes, osteoblasts and chondrocytes (Crisan et al., 2008 Cell Stem Cell, 3:301-313, reviewed by Corselli et al. 2010 Arterioscler Thromb Vasc Biol, 30(6):1104-1109). It is currently accepted that pericytes give rise to or indeed are MSC.

In contrast, other work has shown that pericytes around freshly formed vessels express haematopoietic markers like leukocyte marker CD45 and monocyte marker CD11b in various models of induction of angiogenesis (Rajantie et al. 2004, Ozerdem et al. 2005). Song et al. (2009) demonstrated that pericytes express the haematopoietic progenitor cell marker stem cell antigen-1 (Sca-1), however they could not detect the expression of CD1 lb (Song et al. (2009) Cancer Res, 69(15):6057-6064). This difference is likely due to different time points of sample analysis (2 weeks and 4 weeks post angiogenic induction, respectively). In a matrigel plug assay Tigges et al. found that pericytes not only direct vessel formation (as described above) but also express haematopoietic progenitor cell markers CD34 and Sca-1, and pan leukocyte marker CD45, during early stages of angiogenesis (Tigges et al (2008) Development, 135(3):352-332). These markers were lost in later stages. In addition, more than half of the cells expressing pericyte marker NG2 also expressed macrophage marker F4/80. Cells expressing only NG2 or F4/80, respectively, were also present. This indicates that pericytes recruited during blood vessel formation are of haematopoietic and more specifically, monocytic origin. These diverging views in the literature indicate that different research groups might have described different pericyte populations.

While protocols for pericyte isolation from mature tissues are established, described herein is a way to isolate or generate pericyte progenitors from peripheral blood. As shown herein, this cell population differs from isolated mature pericyte and plays a key role in the onset of angiogenesis. Therefore pericyte progenitors are the ideal cells for therapeutical angiogenesis or anti-cancer therapy.

Remarkably, cells of monocytic origin that show mesenchymal features were described twice; in the early 90's as blood-borne mesenchymal progenitor cells, and a decade later as activated monocytes (Bucala et al. (1994) Mol Med, 1(1):71-81; Kuwana et al. (2003) J Leukoc Biol, 74(5):833-845; Zhao et al. (2003) Proc Natl Acad Sci USA, 100(5): 2426-2431). Surprisingly, peripheral blood, an easily obtainable cell source, was marginalised by a huge body of work on bone marrow-derived MSC's and mesenchymal progenitor cells, respectively. One likely reason is that the culture conditions for bone marrow-derived progenitors were better tunable to generate large numbers of desired cells while peripheral blood work hit a road block in this regard. Pericytes have long been known as cells that are associated with the walls of small blood vessels including those of the blood-brain barrier. What they are and what they are capable of as potential progenitors is beginning to dawn on the stem cell field (Crisan et al. (2008) Cell Stem Cell, 3:301-313). However, they have to be purified from microvasculature-rich homogenised tissue (e.g. from muscle, placenta).

Described herein is the use of a key biotechnology platform to generate clinically relevant numbers of pericyte like cells with an angiogenic potential in vivo for the treatment of ischemic disease, and potentially, some cancers. The platform enables the generation of about 40 million pro-angiogenic cells from a single blood donation (e.g., a blood donation, or unit of blood, of ~400 ml) after one week of cell culture without additional growth factors—5 fold more than the most current protocols can generate as blood-borne mesenchymal progenitor cells (Kuwana et al. 2003 J Leukoc Biol, 74(5):833-845).

Specifically, described herein is the generation and propagation of pericyte progenitors (also referred to herein as pericyte progenitor cells) from peripheral blood. Using a biotechnological platform of macromolecular crowding (MMC), fibronectin coated wells and crude buffy coat cultures, spindle and polygonal shaped cells expressing platelet derived growth factor-1 (PDGFR-1) and neuron-glial antigen (NG2) were generated in clinically relevant numbers. As shown herein, 40 million pericyte progenitors could be generated from one blood donation (400 ml) in one week. Interestingly, the pericyte progenitors did not express HLA-DR indicating the loss of host defense properties of monocytes and macrophages. When co-cultured with human ubilical vein endothelial cells (HUVEC), the pericyte progenitors colocalized with the capillary tubes formed and attained pericyte locations. They were neatly attached along the tubes and loosely associated with sprouting points. When co-culture experiments were repeated with mesenchymal stem cells no tubes but only cell aggregates were formed. Monoyte-derived macrophages failed to co-localize with forming capillary networks. Also shown herein is that pericyte progenitors enhanced endothelial sprouting and supported endothelial survival during sprouting. The pericyte progenitors expressed pro-angiogenic factors, which enhance capillary sprouting directly and through the stimulation of endothelial cells. Methods described herein use peripheral blood to generate pericytes for revascularisation strategies, a minimally invasive procedure with low risk and from a renewable source. As described in further detail herein, macromolecular crowding was used to drive up the pericyte progenitor cell count by 5 to 6 fold.

Thus, provided herein are pericyte progenitor cells (e.g., isolated pericyte progenitor cells), methods for generating pericyte progenitors in clinically relevant numbers for various applications applying macromolecular crowding during cell culture, and methods of using the pericyte progenitor cells. For example, these cells can be obtained in an autologous fashion in a clinically relevant time frame, which opens up new avenues for autologous cell therapy e.g., for treatment of ischemic tissue.

Accordingly in one aspect, the invention is directed to isolated pericyte progenitor cells. Depending upon the time of isolation, the pericyte progenitors express only one or more markers described herein (some (e.g., two or more) of the markers; only some (e.g., two) of the markers). Thus, the isolated pericyte progenitor cells can comprise, consist essentially of, or consist of one or more of the markers described herein.

In one aspect, the invention is directed to isolated pericyte progenitor cells which express platelet-derived growth factor β (PDGFR-β) and neuron-glial antigen 2 (NG2). In another aspect, the invention is directed to isolated pericyte progenitors which express one or more markers described herein. In a particular aspect, the invention is directed to isolated pericyte progenitors which express platelet-derived growth factor β (PDGFR-β), neuron-glial antigen 2 (NG2), Tie-2, vascular endothelial growth factor receptor-1 (VEGFR-1), VEGFR-2 or a combination thereof. In yet another aspect, the isolated pericyte progenitor cells can further express a smooth muscle action (α-SMA), desmin, CD206, CD29, one or more pro-angiogeic factors, or a combination thereof. Examples of pro-angiogenic factors which the pericyte progenitors express include granulocyte macrophage colony stimulating factor (GM-CSF), vascular endothelial growth factor (VEGF), interleukin-8 (IL-8), CXC16, matrix metalloproteinase-9 (MMP-9), urokinase type plasminogen activator (uPA), monocyte chemoattractant protein-1 (MCP-1) or a combination thereof.

In a particular aspect, the isolated preicyte progenitor cells do not express human leukocyte antigen-DR (HLA-DR), collagen I, CD144, CD90, von Willebrand Factor(vWF), CD73, CD166 or a combination thereof. As described herein the isolated progenitor cells can home (migrate) to blood vessels and co-localize at sprouting points (growth points) of blood vessels. In a particular aspect, the isolated pericyte progenitor cells are human pericyte progenitor cells. The isolated pericyte progenitor cells can further comprise a detectable tag.

As used herein, "isolated," "substantially pure," "substantially pure and isolated" or "a homogeneous population of" pericyte progenitor cells, refer to cells that are separated from, or substantially isolated with respect to, the complex cellular milieu in which the cells naturally occur, or the culture medium when produced by recombinant techniques, or chemical precursors or other chemicals when chemically synthesized. In other instances, the isolated material will form part of a composition (for example, a crude extract containing other substances), buffer system, or reagent mix. In yet other circumstances, the material may be purified to essential homogeneity, for example, as determined by flow cytometry, gel electrophoresis and the like. Preferably, isolated pericyte progenitor cells comprise at least about 50%, 80%, 90%, 95%, 98% or 99% (on a molar basis) of all macromolecular species present.

In another aspect, the invention is directed to a method of obtaining pericyte progenitor cells comprising culturing blood cells with a matrix to which cells can attach and one or more organic-based hydrophilic macromolecules, thereby producing a cell culture. The cell culture is maintained under conditions in which pericyte progenitor cells are generated (e.g., expanded, increased) in the cell culture, thereby obtaining pericyte progenitor cells.

In particular aspects, the blood cells used in the methods of obtaining the pericyte progenitor cells are white blood cells (e.g., lymphocytes, monocytes, macrophages). In one aspect, the white blood cells are peripheral blood mononuclear cells (PBMCs, e.g., isolated PMBCs). PMBCs can be obtained, for example, from commercial sources or obtained from (e.g., isolated) a source in which they normally occur, such as a biological sample (e.g., a biological fluid or tissue). In a particular aspect, the PMBCs are obtained from blood (e.g., a blood sample from one or more individuals (e.g., one or more samples from a blood bank); a blood sample from an individual to whom the pericyte progenitors will be administered) using methods routine to those of skill in the art. For example, as described herein, PMBCs can be obtained from the buffy coat layer of a blood sample (e.g., an anti-coagulated blood sample) via density gradient centrifugation (e.g., FicollPaque™).

The blood cells can be contacted with the matrix and one or more macromolecules at a variety of seeding concentrations. In a particular aspect, the blood cells can be contacted with the matrix and one or more macromolecules at about 10,000 cells/cm$^2$ to about 1,000,000 cells/cm$^2$; about about 50,000 cells/cm$^2$ to about 800,000 cells/cm$^2$; or about 100,000 cells/cm$^2$ to about 500,000 cells/cm$^2$ etc.

In other aspects, the blood cells are mammalian cells. For example the blood cells can be primate (e.g., human), canine, feline, bovine, equine, and the like.

As noted herein, the pericyte progenitor concentration in a sample (e.g., a blood sample) can be increased about 5-fold to about 6-fold using the methods described herein. Thus, in particular aspects, the pericyte progenitor cell count in a sample can be increased by about 2-fold, 3-fold, 4-fold, 5-fold, or 6-fold using the methods described herein. In a particular aspect, 100,000 pericyte progenitor cell per 1 ml of blood is obtained. In another aspect, about 40 million pericyte progenitor cells can be obtained from a single unit of donated blood (e.g., about 400 ml blood).

In the methods of the invention, the blood cells are cultured with a matrix (scaffold) to which the cells can attach during culture. As known to those of skill in the art, there are a variety of biologically compatible matrices used for culturing cells. The matrix can be used as a thin coating on tissue-culture surfaces (e.g., culture plates, wells) to promote attachment, spreading, and proliferation of a variety of cell types. Examples include extracellular matrices, hydrogels and polymer scaffolds (e.g., polyethylene glycol (PEG) scaffolds). In one aspect, the matrix is all or a portion of an extracellular matrix (ECM). ECMs can be composed of proteins such as collagen and elastin that serve as scaffolds for cells, as well as networks of various adhesion ligands and growth factors. ECMs can be naturally occurring (e.g., extracted) ECMs, engineered (e.g., synthetic) ECMs or a combination thereof. In a particular aspect, and as exemplified herein, the matrix comprises fibronectin, a high-molecular weight glycoprotein of the extracellular matrix typically found in interstitial matrix and plasma.

In the methods of the invention, the cells are contacted with one or more organic-based hydrophilic macromolecules, also referred to herein as a crowder macromolecule or a macromolecular crowder. In one aspect, the cells are contacted with two or more (at least two) carbohydrate-based macromolecules, referred to herein as mixed macromolecular crowding. In particular aspects, the cells are contacted with multiple, e.g., two, three, or four, etc. organic-based hydrophilic macromolecules.

A characteristic of the microenvironment of all cells is the high total concentration of macromolecules. Such media are termed 'crowded' rather than 'concentrated' because, in general, no single macromolecular species occurs at high concentration but, taken together, account for a volume occupancy of 20-30% of a given specific volume. As pointed out by Ellis (2001) and Minton (2000) crowding by macromolecules has both thermodynamic and kinetic effects on the properties of other macromolecules that are not generally appreciated (Minton, AP, Curr Biol, 10(3):R97-9 (2000); Ellis, R J, Trends Biochem Sci, 26(10):597-604 (2001)). Biological macromolecules such as enzymes have evolved to function inside such crowded environments. For example, the total concentration of protein and RNA inside bacteria like E. coli is in the range of 300-400 g/l. Macromolecular crowding causes an excluded volume effect (EVE), because the most basic characteristic of crowding agents is the mutual impenetrability of all solute molecules. This non-specific steric repulsion is always present, regardless of any other attractive or repulsive interactions that might occur between the solute molecules. Thus, crowding is an inevitable hallmark of the intracellular milieu of all carbon-based life-forms on earth (reviewed in Ellis, R J, *Trends Biochem Sci*, 26(10):597-604 (2001)). The effects resulting from macromolecular crowding are so large that authorities in the field state that many estimates of enzyme catalyzed reaction rates and equilibria made with uncrowded solutions in the test tube differ by orders of magnitude from those of the same reactions operating under crowded conditions within cells (Ellis, R J, *Trends Biochem Sci*, 26(10):597-604 2001).

Despite this knowledge, biochemists still commonly study enzymatic reactions in solutions with a total macromolecular concentration of 1-10 g/l or less, in which crowding is negligible. A particular example is the polymerase chain reaction which is performed in a diluted aqueous environment. If crowdedness in introduced into such a system emulating an intracellular environment, the kinetics shift dramatically, the reaction is accelerated, more amplicons are generated, the enzyme is heat-protected, and primer-template interactions are enhanced (Lareu, R R, et al., *Biophy Biochem Res Comm*, 363(1):171-177 (2007c), Harve, K S, et al., *Nucleic Acids Res*, epub (Oct. 23, 2009), Raghunath, M et al. WO 2008/018839 A1, all of which are herein incorporated by reference).

The principle of macromolecular crowding also reigns in the extracellular environment. Cells are surrounded by soluble and immobilised macromolecules which form their native microenvironment. Again, contemporary cell culture consists of placing adhering cells on a support (tissue culture plastic or other materials) or keeping them in suspension in aqueous media under conditions that do not reflect the crowded environment from which they have been originally derived. Thus, they cannot exert they physiological function to the fullest potential. In fact, it has been shown that when fibrogenic cells are grown under crowded conditions using negatively charged crowders, enzymatic steps are accelerated that control the deposition rate of collagen (Lareu, R R., et al., *Tissue Engineering*, 13(2):385-391 (2007a); Lareu, R R., et al., *FEBS Lett*, 58/(14):2709-2714 (2007b)).

As used herein "macromolecular crowders" are inert macromolecules and can be of any shape (e.g., spherical shape), and are typically of neutral or negative surface charge with a molecular weight above about 50 kDa (see WO 2011/108993, which is herein incorporated by reference). In a particular aspect, the macromolecules are carbohydrate based. The macromolecules according to the invention may have a Molecular weight of from about 50 kDa to about 1000 kDa. In specific aspects, the molecular weight of the macromolecule is about 50, 100, 200, 300, 400, 500, 600, 700, 800, 900, or 1000 kDa. In a particular aspect, the organic-based macromolecule according to the invention is a carbohydrate-based hydrophilic macromolecule. For example, the carbohydrate-based macromolecule of the invention may be a polymer of glucose and/or sucrose. Particular examples of the macromolecule according to the invention include Ficoll™70, Ficoll™400, polyvinyl pyrrolidone (PVP), glycosaminoglycans, sugar chains of glycosaminoclycans, cellulose, pullulan or a mixture thereof. Specifically, the carbohydrate-based macromolecule can be Ficoll™70, Ficoll™400, dextran, neutral dextran (neutral dextran 410; neutral dextran 670, PVP 360 kDa, pullulan, dextran sulfate, polystyrene sulfonate, chondroitan sulfate, heparin sulfate, heparin sulfate; dermatan sulfate or a mixture thereof. In particular aspects, the carbohydrate-based hydrophilic macromolecule is Ficoll. In yet another aspect, the macromolecular crowder used in the method is a mixture of Ficoll™70 and Ficoll™400. Ficoll can be obtained from commercial sources such as Amersham Biosciences as Ficoll™70 (Fc70; 70 kDA) under catalogue number 17-0310 and Ficoll™400 (Fc400; 400 kDa) under catalogue number 17-0300.

In other aspects, of the methods provided herein, the solution containing the macromolecule according to the invention may have a viscosity of less than about 2 mPa-s. For example, a viscosity of about 1.75 mPa-s, 1.5 mPa-s, 1.25 mPa-s, 1 mPa-s 0.75 mPa-s, 0.5 mPa-s, or 0.25 mPa-s.

In yet other aspects, the macromolecule can have a hydrodynamic radius range of from about 2 nm to about 50 nm, from about 5 nm to about 20 nm or from about 10 nm to about 15 nm.

In some aspects, the total macromolecular concentration is about 2.5-100 mg/ml, and in other aspects, about 5-90 mg/ml, about 10-80 mg/ml, about 20-70 mg/ml, about 30-60 mg/ml, about 40-50 mg/ml, and in yet other aspects about 10-40 mg/ml, about 10-62.5 mg/ml, or about 10-37.5 mg/ml. In particular aspects, the macromolecule may be Ficoll™70 present at a concentration of 2.5-100 mg/ml, and/or Ficoll™400 at a concentration of 2.5-100 mg/ml, or a mixture thereof. In other particular aspects, the macromolecule may be Ficoll™70 present at a concentration of 2.5-37.5 mg/ml and/or Ficoll™400 at a concentration of 2.5-25 mg/ml, or a mixture thereof. In a particular aspect, the stem cells are contacted with a carbohydrate-based macromolecule comprising Ficoll™70 at a concentration of about 37.5 mg/ml and Ficoll™400 at a concentration of about 25 mg/ml.

The concentration of macromolecules for use in the present invention can also be calculated based on the volume fraction occupancy. As known to those of skill in the art, the composition of a solution containing very large molecules (macromolecules) such as polymers, is most conveniently expressed by the "volume fraction ($\Phi$)" or "volume fraction occupancy" which is the volume of polymer used to prepare the solution divided by the sum of that volume of macromolecule and the volume of the solvent. In the methods described herein the cells are contacted with the one or more macromolecules at a biologically relevant volume fraction occupancy. In some aspect, the biologically relevant volume fraction occupancy is from about 3% to about 30%. In other aspects, the biologically relevant volume fraction occupancy is from about 5% to about 25%, from about 10% to about 20% and from about 12% to about 15%. Thus, in the methods of the invention, the volume fraction occupancy is about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30%. In a particular aspect, the biologically relevant volume fraction occupancy is about 15%.

The macromolecule can be added to the cell culture in a variety of ways. For example, the macromolecules are added as a powder or liquid into culture medium. Preferably, the addition of the macromolecule does not significantly increase the viscosity of the cell culture medium. The medium can then be sterilized, e.g. via filtration, if desired. In one aspect, the crowding cocktail contains a combination of Fc 70 and Fc 400.

As will be appreciated by those of skill in the art, additional macromolecular crowders can be added to the cell culture medium. In one aspect, the additional crowder(s) is either a neutrally charged crowder (e.g., PVP) or a negatively charged crowder (e.g., Dextran sulfate 500 kDa) (e.g., see WO 2011/108993, which is herein incorporated by reference).

In particular aspects, the method comprises contacting the cells with at least two organic-based hydrophilic macromolecule of neutral surface change. In other aspects, the method comprises contacting the cells with (a) at least two organic-based hydrophilic macromolecule having a molecular weight of 50 kDa to 1000 kDa and neutral surface charge, or (b) at least one organic-based hydrophilic macromolecule having a radius range of 2 to 50 nm and neutral surface change, or (c) at least two organic-based hydrophilic macromolecule having a molecular weight of 50 kDa to 1000 kDa and neutral surface charge combined with a third organic-based hydrophilic macromolecule having a molecular weight of 50 kDa to 1000 kDa and neutral surface, or (d) at least two organic-based hydrophilic macromolecule having a molecular weight of 50 kDa to 1000 kDa and neutral surface charge combined with a third organic-based hydrophilic macromolecule having a molecular weight of 50 kDa to 1000 kDa and having a negative or neutral surface charge.

The method of obtaining pericyte progenitor cells can further comprise detecting pericyte progenitor cells in the cell culture. A variety of methods can be used to detect pericyte progenitors. In one aspect, the method for detecting pericyte progenitor cells comprises detecting cells which adhere to the matrix and express platelet-derived growth factor $\beta$ (PDGFR-$\beta$), neuron-glial antigen 2 (NG2), Tie-2, vascular endothelial growth factor receptor-1 (VEGFR-1), VEGFR-2, CD206 or a combination thereof.

As shown herein, the cells are maintained under conditions in which pericyte progenitor cells are generated (proliferate, expand, increase) in the cell culture (e.g., the concentration of pericyte progenitor cells are increased in the cell culture compared to when the blood cells were not contacted with the matrix, the macromolecular crowders and/or maintained under suitable conditions). A variety of methods for maintaining the cell culture under conditions in which the pericyte progenitor cells proliferate can be used and are known to those of skill in the art. Such methods include introducing agents such as serum (e.g., fetal bovine serum (FBS) or human serum), growth factors, antibiotics and the like into the culture, maintaining the cell culture under serum starved conditions or in an expansion medium etc. As used herein, the expression "proliferation" or "proliferating" is used in its regular meaning and relates to the expansion of cells or tissue, including cell growth and cell division. The term "maintenance" as used herein in relation to the culture of pericyte progenitor cells, refers to the preservation of the "progenitorness" of the cells in culture.

Those of skill in the art will appreciate that a variety of suitable conditions can be used. In a particular aspect, the conditions under which the cell culture is maintained comprise maintaining the cell culture at about 37° C. in an atmosphere of about 5% CO2/95% air. As will also be appreciated by those of skill in the art, the cell culture conditions can be occur in a number of environments such as a 2-dimensional (2D) and/or 3-dimensional (3-D) environment.

The cells can be cultured for any number of days and will depend upon the desired outcome (e.g., the desired concentration of pericyte progenitor cells). In a particular aspect, the cells are cultured for about 3 days to about 180 days, about 3 days to about 90 days, about 3 days to about 60 days, about 3 days to about 30 days, about 3 days to about 15 days, or about 3 days to about 7 days.

The method of obtaining pericyte progenitor cells can further comprise isolating the pericyte progenitor cells from the combination using any variety of methods known in the art. In a particular aspect, the pericyte progenitor cells are isolated by harvesting cells which adhere to the matrix and express platelet-derived growth factor β (PDGFR-β), and neuron-glial antigen 2 (NG2), Tie-2, vascular endothelial growth factor receptor-1 (VEGFR-1), VEGFR-2, CD206 or a combination thereof.

In another aspect, the invention is directed to pericyte progenitor cells produced by the methods described herein. As will be appreciated by those of skill in the art, the pericyte progenitor cells can comprises a label that can be detected directly or indirectly (a detectable label) using a variety of techniques known to those of skill in the art. A variety of labels that can be attached to a cell and thereby capable of being detected are known to those of skill in the art and include fluorescent labels (e.g., green fluorescent protein), bioluminescent labels, biotin, streptavidin and the like.

In yet another aspect, the invention is directed to a pharmaceutical composition comprising the pericyte progenitor cells described herein. In a particular aspect, the pharmaceutical composition comprises detectably labeled pericyte progenitor cells.

The pericyte progenitor cells described herein can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The pericyte progenitor and pharmaceutical compositions thereof can be administered systemically and/or locally. Methods of introduction of these compositions include, but are not limited to, intradermal, intramuscular, intraperitoneal, intraocular, intravenous, subcutaneous, topical, oral and intranasal. Other suitable methods of introduction can also include gene therapy, rechargeable or biodegradable devices, particle acceleration devises ("gene guns") and slow release polymeric devices. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The present invention provides methods of generating and propagating pericyte progenitors from peripheral blood under optimum crowding conditions, and the pericyte progenitor cells have a variety of uses, which include the use of the cells for research; culturing for enhancement of cell numbers; or modulating, modifying, labeling and/or expanding prior to administration (re-administration) into a patient for treatment.

For example, the pericyte progenitors generated and/or propagated using the method described herein can be used in regenerative medicine (e.g., regenerative tissue therapy), the treatment of ischemic injuries like stroke, myocardial infarction, congestive heart failure and perivascular disorders.

The conditions of treatment range from chronic venous or artierla ulcer, critical limb ischemia, myocardial infarction to stroke and diabetic neuropathy. The generated cells are brought into suspension and then directly injected into tissue requiring repair and angiogenesis. In other aspects these cells can be delivered in hydrogel (preferably, but not exclusively collagen or hyaluronic acid, or PEG-based hydrogels). In other aspects, cells are delivered systemically into the body via intravenous infusion. In another aspect, cells are delivered to the site of repair via intraarterial injections or catheter-guided application. In another aspect, cells are embedded into an implantable biomaterial (this also can be an advance wound care material) and applied directly to the repair site. In yet another aspect, generated cells are loaded with anticancer drugs, drug-loaded nanoparticles, or antibodies that carry anticancer drugs or pro-drugs and are injected into the arterial blood stream proximal of a tumor for the delivery of bespoke drugs. In another aspect, generated pericytes are loaded with contrasting nanoparticles for detection via MRI or PET for the imaging of repair tissue and cancer.

In a particular aspect, the invention is directed to a method of enhancing growth of one or more blood vessels (angiogenesis) in an individual in need thereof comprising administering pericyte progenitor cells to the individual, thereby enhancing sprouting and survival of the one or more blood vessels in the individual. The pericyte progenitors can be administered systemically, wherein the pericyte progenitors will home or migrate to the site of blood vessel growth, and/or locally at the site of blood vessel growth in the individual.

The pericyte progenitor cells that are administered to an individual can be pericyte progenitors that have been generated from the individual's own blood (administration of autologous pericyte progenitor cells), pericyte progenitors that have been generated from the blood of one or more other individuals (administration of allogenic pericyte progenitor cells) or a combination thereof.

The individual to whom the pericyte progenitors are administered can have a wound, an ischemic injury or a combination thereof.

In another aspect, the invention is directed to a method of detecting one or more sites of angiogenesis in an individual in need thereof comprising detecting pericyte progenitor cells in the individual, wherein one or more sites at which the pericyte progenitor cells is detected is an indication of angiogenesis at the one or more sites in the individual. In a particular aspect, the method can further comprise administering detectably labeled pericyte progenitor cells to the individual and detecting the detectably labeled progenitor pericytes in the individual. The detectably labeled pericyte progenitors will migrate to a site of angiogenesis that is occurring such as at a site of a tumor, a site of tissue regeneration, a site of ischemic injury, a site of a wound or a combination thereof in the individual.

In yet another aspect, the invention is directed to a method of homing an agent to a site (causing or directing an agent to migrate to a site) of angiogenesis in an individual in need thereof, comprising administering the agent to the individual wherein the agent is attached to one or more pericyte progenitor cells which home to a site of angiogenesis in the individual, thereby delivering the agent to the site of angiogenesis in the individual. In a particular aspect, the pericyte progenitor cells further comprise a detectable label. The pericyte progenitors migrate to a site of angiogenesis that is occurring at a site of a tumor, a site of tissue regeneration, a site of ischemic injury, a site of a wound or a combination thereof in the individual.

Thus, the methods of use herein employ the use of pericyte progenitors which can be "loaded" with one or more agents such as nanoparticles that give a signal in a scanner (e.g., an MRI, a CT or other mean of detection) to visualize tumors and/or regenerate tissue, the site where vascularization (or revascularization) will occur.

As used herein an "individual" refers to an animal, and in a particular aspect, a mammal. Examples of mammals include primates, canines, felines, rodents, bovines, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined upon consideration the use of well known risk factors. The effective amount of a (one or more) particular is determined, in the final analysis, by the physician in charge of the case, but depends on factors such as the exact blood vessel and/or condition (e.g., disease) to be treated, the severity of the condition from which a patient suffers, the chosen route of administration, other drugs and treatments which the patient may concomitantly require, and other factors in the physician's judgment.

An effective amount of pericyte progenitors is delivered to an individual in need thereof. As used herein, "effective amount" or "therapeutically effective amount" means an amount of the active that will elicit the desired biological or medical response in a tissue, system, subject, or human, which includes alleviation of the symptoms, in whole or in part, of the condition (e.g., disease) being treated.

Any suitable route of administration can be used, for example, oral, dietary, topical, transdermal, rectal, parenteral, intraarterial, intramuscular, subcutaneous injection, intradermal injection), inhalation (e.g., intrabronchial, intranasal or oral inhalation, intranasal drops), ocular, pulmonary, nasal, and the like may be employed. In one aspect, administration is local, and in other aspects, administration is systemic. The preferred mode of administration can vary depending on the particular agent chosen.

The pericyte progenitors can be administered in a single dose (e.g., in a day) or in multiple doses. In addition, the pericyte progenitors can be administered in one or more days (e.g. over several consecutive days or non-consecutive days).

There is also provided kits for pericyte progenitor generation and propagation for improving the efficiency, activity and/or stability of pericyte progenitors in vitro or ex vivo. For example, the kit can comprise at least two organic-based hydrophilic macromolecule of neutral surface charge, and optionally a third neutral or negatively charged macromolecule. In particular, the kit according to the invention may be a kit for boosting the efficiency, activity and/or stability comprising (a) at least two organic-based hydrophilic macromolecule of molecular weight 50 kDa to 1000 kDa and neutral surface charge, or (b) at least two organic-based hydrophilic macromolecule of radius range of 2 to 50 nm and neutral surface charge; or (c) and optionally at least one more organic-based hydrophilic macromolecule of radius range of 2 to 50 nm and neutral surface charge; or negative charge. The macromolecule used in the kit of the invention is as defined throughout the whole content of the present application.

In another aspect, the invention is directed to a kit for obtaining pericyte progenitor cells from blood comprising a matrix to which blood cells can attach and one or more organic-based hydrophilic macromolecules and instructions for use thereof. The blood cells can be, for example, peripheral blood mononuclear cells (PBMCs) and the one or more organic-based hydrophilic macromolecules comprise one or more carbohydrate-based hydrophilic macromolecules. In particular aspect, the one or more carbohydrate-based macromolecules is a polymer of glucose, sucrose or a combination thereof. The polymer can be, for example, Ficoll™70, Ficoll™400, polyvinyl pyrrolidone (PVP 360 kDa), dextran (neutral dextran 410 kDa; neutral dextran 670 kDa), dextran sulfate, polystyrene sulfonate, pullulan, chondroitan sulfate, heparin sulfate, heparin sulfate, dermatan sulfate or a combination thereof.

EXEMPLIFICATION

Material & Methods
a) Generation of Pericyte Progenitors from Peripheral Blood

Peripheral blood was obtained from the National University Hospital blood bank or from healthy donors. Peripheral blood mononuclear cells (PBMC) were isolated via gradient centrifugation over Ficollpaque (Sigma) following the manufacturer's instructions. Blood was diluted with the same amount of phosphate buffered saline (PBS) containing 2M EDTA. 22 ml of diluted blood were layered over 14 ml of Ficoll-Paque™ and centrifuged at 400 g for 30 min. Buffy coat ring was collected from separated blood samples and washed twice with PBS containing 2 mM EDTA. PBMC were seeded on fibronectin (derived from bovine plasma, Sigma)-coated dishes at a concentration of 2 g/cm$^2$ seeding area in low glucose Dulbecco's modified Eagle's medium (LG DMEM, Gibco-BRL) supplemented with Glutamax, 10% fetal bovine serum, 100 units/ml penicillin and 100 µ/ml streptomycin. Crowding is effected by the addition of a crowding cocktail (Fc-cocktail). Therefore media was supplemented with a cocktail of macromolecules Ficoll™70 (Fc70; Sigma-Aldrich, St Louis) at 37.5 mg/mL and Ficoll™400 (Fc400; Sigma-Aldrich, St Louis) at 25 mg/ml. Cells were maintained at 37° C. in a humidified atmosphere of 5% CO2/95% air. Culture medium was changed after 1-3 days. Spindle shaped cells resembling pericyte progenitors evolved during the first week. Cells were harvested using 0.5% trypsin/lmM EDTA after 1 week.
b) Flow Cytometry Analysis of Pericyte Precursors Adherent cells were harvested from culture dishes, resuspended in PBS buffer supplemented with 0.5% fetal bovine serum (FBS) and incubated with FITC- or PE-conjugated antibodies (BD sciences) directed against the markers shown in FIG. 2 for 30 min. Cells were washed once with PBS buffer supplemented with 0.5% FBS and fixed in 1% formaldehyde in PBS. Samples were analyzed with the Cyan flow cytometer (Dako Cytomation).
c) Adherent Cytometry to Assess Number of Adherent Cells after 7 Days (Count of DAPI Stained Nuclei)

Adherent fluorescent cytometry was based on a montage of 9 sites per well taken by a coolSNAP HQ camera attached to a Nikon TE2000 microscope at 2× magnification, covering 83% of total well area. DAPI fluorescence was accessed with a single Dapi filter [Ex 350 nm/Em 465 nm]. The number of stained nuclei was imported into Microsoft Excel, and the mean±SD of the areas was calculated.
d) Immunocytochemistry Staining for PDGF Receptor β Expressed by Pericyte Precursors Monolayers were fixed with 100% ice-cold methanol for 10 mins then blocked with 3% bovine serum albumin (Fluka05488) (BSA) in PBS. Immunofluorescence was carried out using primary antibodies rabbit anti-human PDGFR-β (Chemicon, 1:100). Secondary antibody AlexaFluor 488 chicken anti-rabbit (Molecular Probes, A21441) was used at 1:400 dilution. Cell nuclei were counterstained with 0.5 µg/ml 4',6-diamidino-2-phenylindole (Molecular ProbesD1306) (DAPI). Images were captured with an IX71 inverted fluorescence microscope (Olympus).
e) Induction of Collagen I Secretion and SDS-Page of Pepsin Digested Culture Media and Cell Layer.

After 7 days of culture collagen secretion of pericyte progenitors was induced by supplementing the culture media with 100 mM L-ascorbic acid phosphate (Wako Pure Chemical Industries, Osaka, Japan). After further 7 days culture media were harvested into separate vials, whereas cell layers were washed twice with Hank's balanced salt solution (HBSS) and both culture medium and washed culture plates (without buffer) were digested with porcine gastric mucosa pepsin (2500 U/mg; Roche Diagnostics Asia Pacific, Singapore) in a final concentration of 100 mg/mL. Samples were incubated at room temperature (RT) for 2 h with gentle shaking followed by neutralization with 0.1 N NaOH.

Sodium Dodecyl Sulfate-Polyacrylamide Gel Electrophoresis (SDS-PAGE):

Medium and cell layer samples were analyzed by SDS-PAGE under non-reducing conditions. A small format was used (Mini-Protean 3; Bio-Rad Laboratories, Singapore). Protein bands were stained with the SilverQuestÔ kit (Invitrogen) according to the manufacturer's protocol. Densitometric analysis of wet gels was performed on the GS-8006 Calibrated Densitometer (Bio-Rad) with the Quantity One v4.5.2 image analysis software (Bio-Rad).
f) Quantitative PCR Analysis Total RNA was extracted using RNAeasy single step column spin following the manufacturer's protocol. cDNA was synthesized from isolated mRNA using Superscript reverse transcriptase II. RT-PCR reactions were performed and monitored on a Stratagene real-time PCR instrument (Strategene) with a PCR mix based on Platinum Taq DNA polymerase (Invitrogen). For each cDNA sample, the CT value was defined as the cycle number at which the fluorescent intensity reached the amplification base threshold fixed by the instrument-software. Relative expression levels for collagen I and vWF was calculated by normalizing the quantified cDNA transcript level (Ct) to the house-keeping gene GAP-DH.
g) Tube Formation Assay: Co-Culture of Endothelial Cells and Pericyte Precursors Endothelial cells (human umbilical cord endothelial cells, Lonza) were expanded in EGM-2 culture medium (Lonza) until 5 splits (passage plus 5 (p+5)). 48 well-plates were coated with a thick layer of matrigel (BD) at 150 µl/cm$^2$. Endothelial cells and pericyte precursors were Tabled alive with green or red fluorescence using PKH26 Red and PKH76 Green Fluorescent Cell Linker Kit for General Cell Membrane Labelingkit (Sigma) following the manufacturer's instructions. Endothelial cells were seeded at a seeding density of 20,000 cells per cm$^2$ and pericyte precursors were added at the same timepoint or later at 10,000 cells per cm$^2$. Tubular networks formed over 8 h and were viewed at different timepoints over the next 2 days with an IX71 inverted fluorescence microscope (Olympus). For measuring the total tube length 6 representable pictures at 10× magnifications were taken and total tube length was analyzed using ImageJ software. Life cell imaging of tube formation over a timeframe of 24 h was done using Live Cell Imaging System with Laser TIRF at the SBIC Nikon imaging centre.

Tube formation assay was repeated using macrophages, which were generated from M-CSF induced monocytes isolated from human blood and mesenchymal stem cells at p+5 from Lonza.
h) Spheroid Sprouting Assay Human umbilical vein endothelial cells (HUVECs) with generated pericyte progenitors or alone were seeded into low-adherence round bottom 96-well plates over night in EGM-2 media (Lonza) containing methylcellulose. Cells formed spheroids, which were collected and seeded into collagen I gels from bovine skin (PureCol®) at a concentration of 1 mg/ml. After three days images of sprouted spheroids were taken with an IX71 inverted fluorescence microscope (Olympus). Sprout length was measured using the software ImageJ.

i) Angiogenesis Proteome Array Analysis

Blank media or culture media conditioned by pericyte progenitors was collected after three days and filtered with a 0.22 μm filter. Samples were analyzed using the Proteome Profiler™ Array Human Angiogenesis Array Kit from R&D with the Catalog Number ARY007 using manufacturer's instructions. Intensity of detected antigens was measured using the software imageJ.

Results

Generation of Pericyte Progenitors from Peripheral Blood

When peripheral blood mononuclear cells (PBMC) were seeded in culture medium containing Fc-crowders part of the cells attach to the fibronectin coating. The non-adherent cells were removed during the media change in the first week. The attached cells started to elongate, which could be already observed after 3 days of culture. After 5 days spindle-shaped and polygonal cells were formed, which resembled pericyte progenitors (FIG. 1). About one million of peripheral blood mononuclear cells (PBMCs) were isolated from about one milliliter of blood. After an initial culturing period of 5 to 7 days about 100,000 pericyte progenitors can be generated. A blood donation of about 400 ml can therefore yield in clinically significant numbers of about 40 million pericyte progenitors.

Pericyte Progenitor Marker Expression Determined by Flow Cytometry

Pericyte progenitors were tested for mesenchymal stem cell (MSC) markers CD90, CD29, CD166 and CD73; markers shared by MSC and endothelial cells (EC) CD105 and CD146; EC markers VEGFR-2 and CD14; and hematopoietic markers CD45, CD13, CD34, CD14, CD11b, HLA-DR, CD206, CD83, CD19 and CD117.

Figure 2:
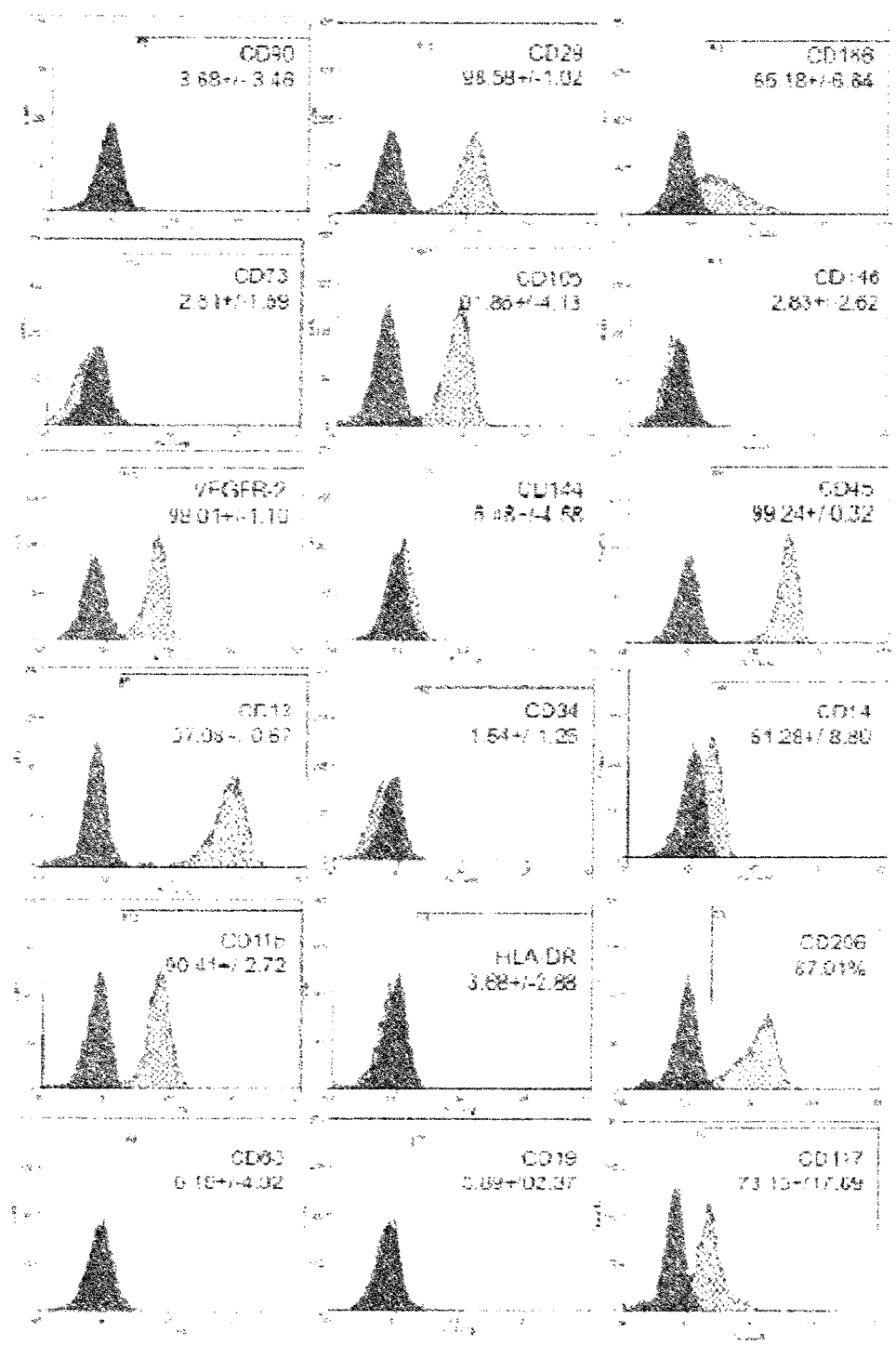
FIG. 2 shows flow cytometry analysis of marker expression by pericyte progenitors. Pericyte progenitors were tested for mesenchymal stem cell (MSC) markers CD90, CD29, CD166 and CD73, markers shared by MSC and endothelial cells (EC) CD105 and CD146, EC markers VEGFR-2 and CD144, hematopoietic markers CD45, CD13, CD34, CD14, CD11b, HLA-DR, CD206, CD83, CD19 and CD117.

Pericyte progenitors differed from MSC demonstrated by the lack of expression of MSC markers CD90 and CD73 (FIG. 2). However, they expressed CD29 (FIG. 2), which is a fibronectin receptor. As fibronectin was used for the isolation and generation of pericyte progenitors, it was selective for CD29+ cells.

The expression of CD105 and VEGFR-2 showed overlapping marker expression with EC (FIG. 2). Still, the essential EC marker CD144 (VE-Cadherin) was not expressed by pericyte progenitors (FIG. 2), indicating that they differ from endothelial cells. VEGFR-2 expression (FIG. 2) indicates a role of pericyte progenitors in angiogenesis, because they are able to respond to VEGF signaling. VEGF is a hallmark growth factor in angiogenesis.

Pan-leukocyte marker CD45 and myeloid marker CD13 confirm the hematopoietic origin of these cells. Partial expression of CD14 and expression of CD11b further demonstrates their monocytic origin (FIG. 2). The lack of HLA-DR (MHC II complex) expression clearly distinguishes generated pericyte progenitors from classical macrophages, as they lack the ability to present antigens by the MHC II complex. CD206, also a marker of generated pericyte progenitors, is expressed often on alternatively activated macrophages, which are monocyte-derived cells differing from the classical macrophages that mediate the first inflammatory response (Mosser and Edwards (2008) Nature Reviews, 8:961) (FIG. 2). These cells were shown to mediate wound healing and angiogenesis in vivo (Mosser and Edwards (2008) Nature Reviews, 8:961). The lack of CD83 and CD19 demonstrated that the culture of pericyte progenitors is not unpurified (contaminated) with other cell types like dendritic cells (CD83-) and B cells (CD19-) (FIG. 2). C-kit (CD117) is a stem cell marker that emphasizes the progenitor character of generated pericyte progenitors (FIG. 2).

Pericyte Progenitors Marker Expression Determined by Immonocytochemistry

Figure 3:
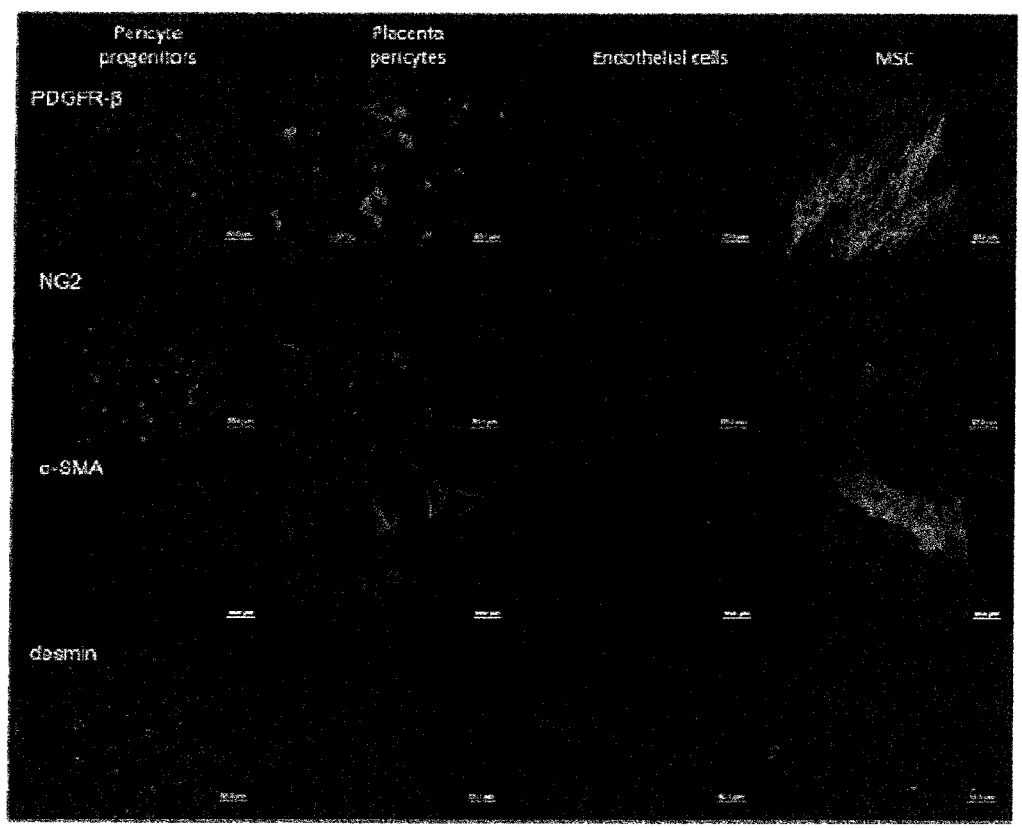
FIG. 3 shows immunocytochemistry staining for human pericyte marker. Pericyte progenitors, EC and placenta-derived pericytes (commercially available from Promocell) and mesenchynmal stem cells (MSC) were stained for early pericyte marker PDGFR-β, NG2 and for later pericyte marker α-SMA and desmin. Generated pericyte precursors express early pericyte markers and are distinguishable from mature pericytes, which were isolated by digestion of human placenta.

Pericyte progenitors, EC and placenta-derived pericytes (commercially available from Promocell) were stained for early pericyte marker PDGFR-β, NG2 and for later pericyte marker α-SMA and desmin. Generated pericyte precursors express early pericyte markers and are distinguishable from mature pericytes, which were isolated by digestion of human placenta (FIG. 3).

PDGFR-β expression was weaker as compared to the expression of mature pericytes isolated from human placenta. The expression of NG2 and desmin was highly variable (from weak to strong) for placenta pericytes, they showed however always a strong staining for α-SMA. Interestingly only the expression of NG2 made them distinguishable from MSC. Generated pericyte progenitors showed a constant expression of NG2. They did not show expression of α-SMA and no to a weak expression for desmin (FIG. 3).

Figure 4:
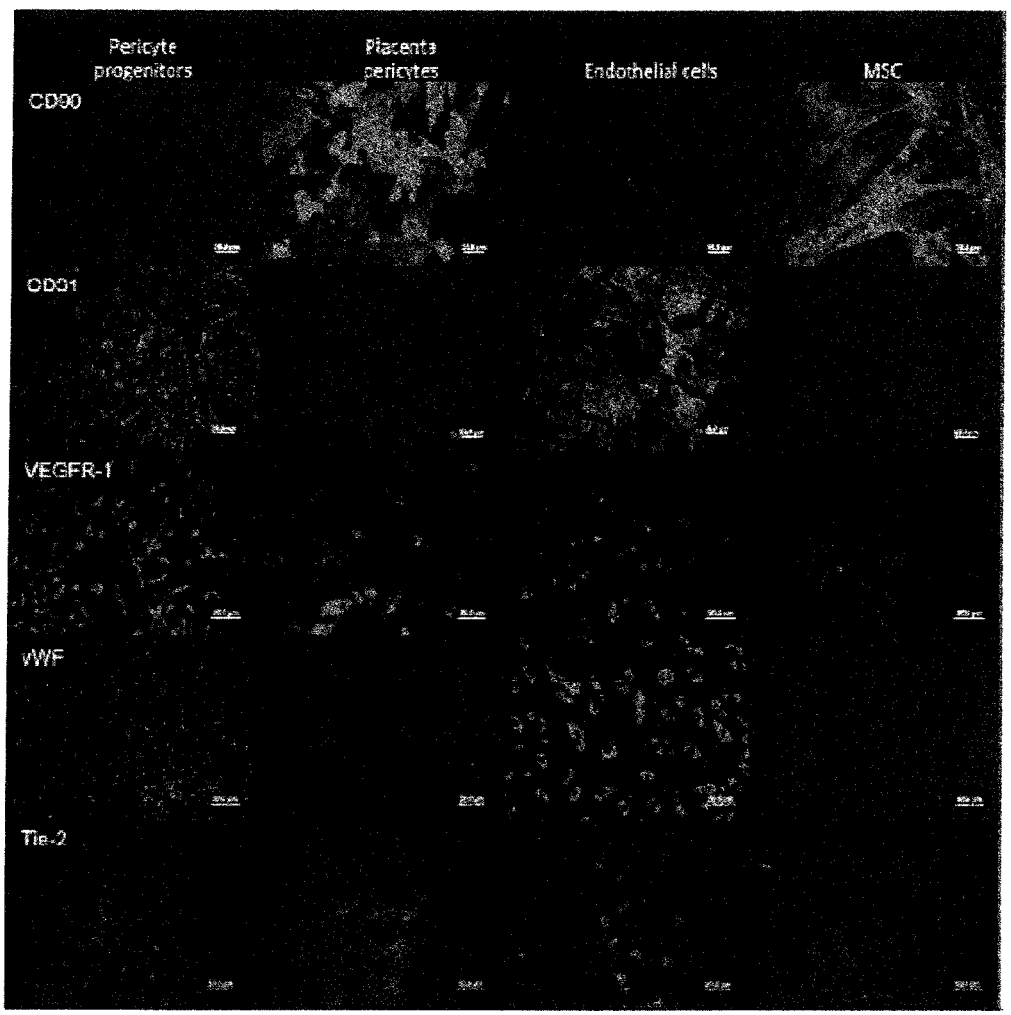
FIG. 4 shows immunocytochemistry staining for MSC and EC markers (40× magnification) of pericyte progenitors, EC and placenta-derived pericytes and MSC.

Confirming the flow cytometry data (FIG. 2), pericyte progenitors did not express MSC marker CD90. Interestingly, generated cells expressed many markers found on endothelial cells. CD31 is not restricted to EC, but is also expressed on platelets and monocytes. In this cell culture not only spindle-shaped cells resembling blood-derived pericyte progenitors but also a pattern of small granules is stained (FIG. 4). These granules most likely resemble platelets. Interestingly a similar pattern is found, when the cell culture is stained for vWF (FIG. 4). Platelets are known to contain vWF. No staining of spindle-shaped cells was observed (FIG. 4).

Both pericyte population expressed VEGFR-1 and Tie-2 and were distinguishable from MSC by their expression (FIG. 4). Both receptors play keyroles in angiogenesis.

Pericyte Progenitors do not Express Collagen I or VWF

Figure 5:
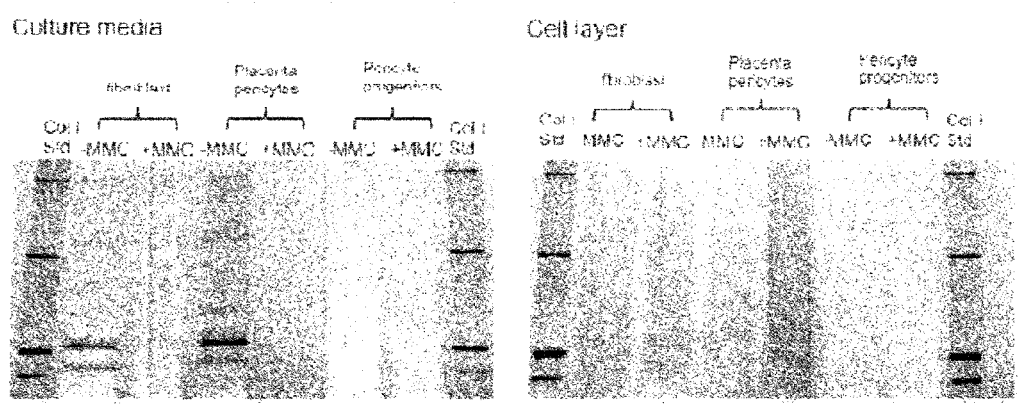
FIG. 5 shows SDS-Page analysis of Collagen I (Col I) secretion by pericyte progenitors. Culture media and cell layer of pericyte progenitors, placenta-derived pericytes and fibroblast (IMR-90) as a positive control were pepsin-digested. As a result only triple-helical structures remained. Medium samples, cell layer samples and a collagen I standard (Col I std) were analyzed by SDS-PAGE under non-reducing conditions. Protein bands were stained with the SilverQuest kit (Invitrogen) according to the manufacturer's protocol. In contrast to fibroblast and placenta-derived pericytes, pericyte progenitors did not secrete any Collagen I.

Pericyte progenitors, placenta pericytes, and fibroblasts (IMR-90) as a positive control were cultured under conditions allowing the secretion of collagen into the culture media. Further in some of the cultures, the same crowders (+MMC) (Ficoll™70 and Ficoll™400) were added to allow the deposition of the secreted collagen. Culture media and cell layer of all cell populations were pepsin-digested, and, as a result, only triple-helical structures remained. Medium samples, cell layer samples and a collagen I standard (Col I std) were analyzed by SDS-PAGE under non-reducing conditions. Protein bands were stained with the SilverQuest kit (Invitrogen) according to the manufacturer's protocol. Mature pericytes derived from placenta secreted collagen I comparable to the secretion of collagen by fibroblasts and were able to deposit it under crowded conditions (+MMC) into the cell layer. In contrast pericyte progenitors from peripheral blood did not secrete any detectable levels of Collagen I or other triple-helical collagens (FIG. 5).

Figure 6:
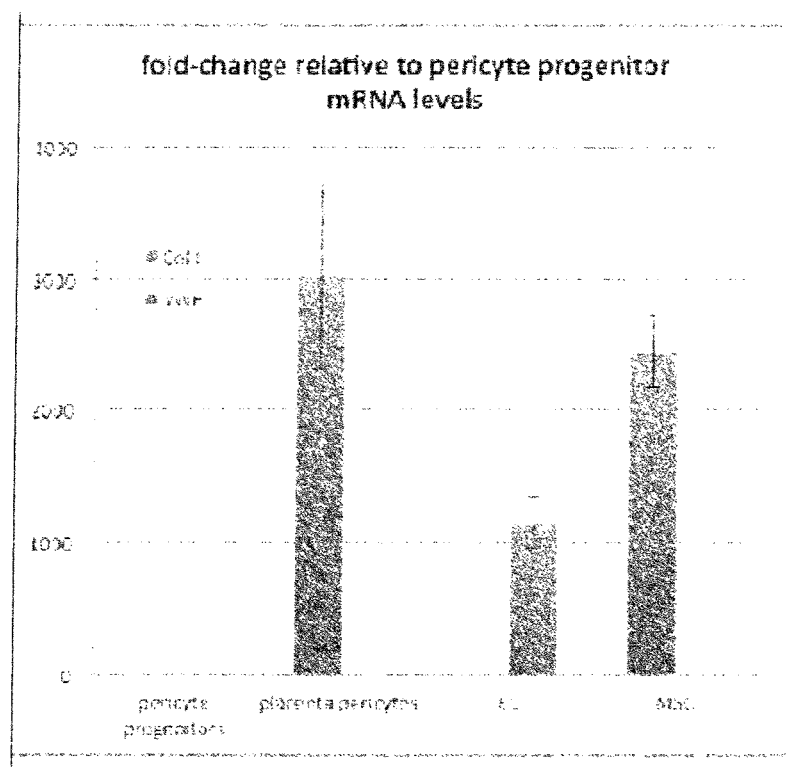
FIG. 6 shows PCR analysis of collagen I and vWF mRNA expression. Pericyte progenitors do not show significant levels of collagen I or vWF mRNA levels.

Pericyte progenitors did not show significant levels of collagen I or von Willebrand Factor (vWF) mRNA levels. Former research describes the generation of another type of blood-derived progenitor cell from peripheral blood called the fibrocyte or activated monocyte (MOMC, φ-macrophages) (Bucala et al. (1994) Mol Med, 1(1):71-81; Kuwana et al. (2003) J Leukoc Biol, 74(5):833-845; Zhao et al. (2003) Proc Natl Acad Sci USA, 100(5):2426-2431). These cells expressed leukocyte and monocyte markers, which are also present on pericyte progenitors. However, the fibrocytes also expressed HLA-DR, which pericyte progenitors did not (FIGS. 2 & 4) and further it was shown that they did not express Collagen I (FIG. 5 and FIG. 6) as it was described for fibrocytes. It was also described before that different populations of EC can be isolated from peripheral blood (Fuchs et al. (2006) Cell Tissue res, 326:79-92). Generated pericyte progenitors did not express CD144 (VECadherin, FIG. 2). In addition no vWF-staining of spindle-shaped cells was detectable by immunocytochemistry (FIG. 4). To further confirm these data PCR showed that only control endothelial cells showed significant levels of vWF (FIG. 6). Therefore, pericyte progenitors are distinguishable (distinct) from other blood-derived progenitors.

Pericyte Precursors co-Localise with Capillary Network

Figure 7:
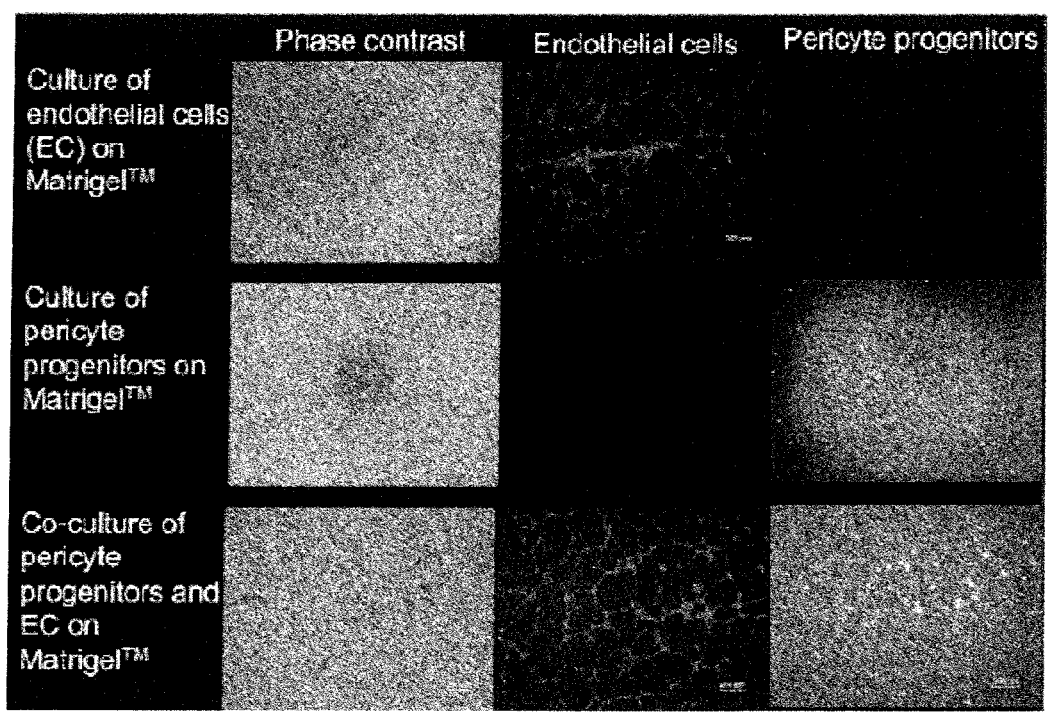
FIG. 7 shows tube formation assay: Co-culture of endothelial cells (life red fluorescent labeling) and pericyte progenitors (life green fluorescent labeling) on matrigel (4× magnification).
Figure 8:
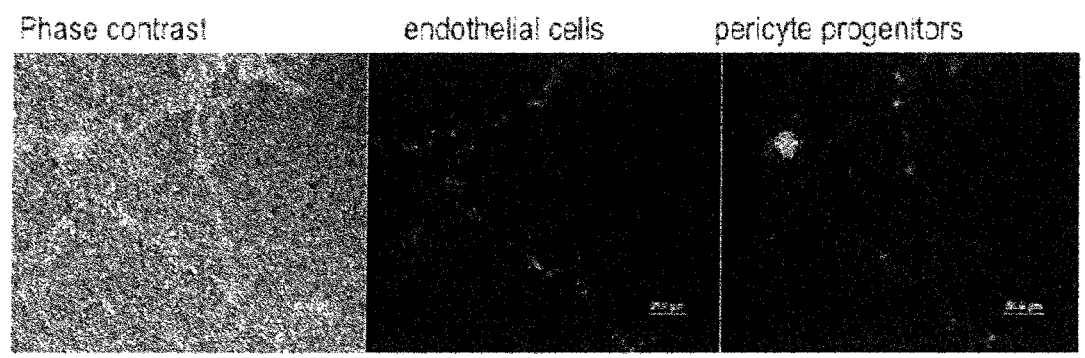
FIG. 8 shows tube formation assay: Co-culture of endothelial cells (life red fluorescent labeling) and pericyte progenitors (life green fluorescent labeling) on matrigel (20× magnification). Pericyte progenitors co-localize with tubes formed by endothelial cells. They are found sparsely distributed over the tubes and often accumulate at junction points.
Figure 9:
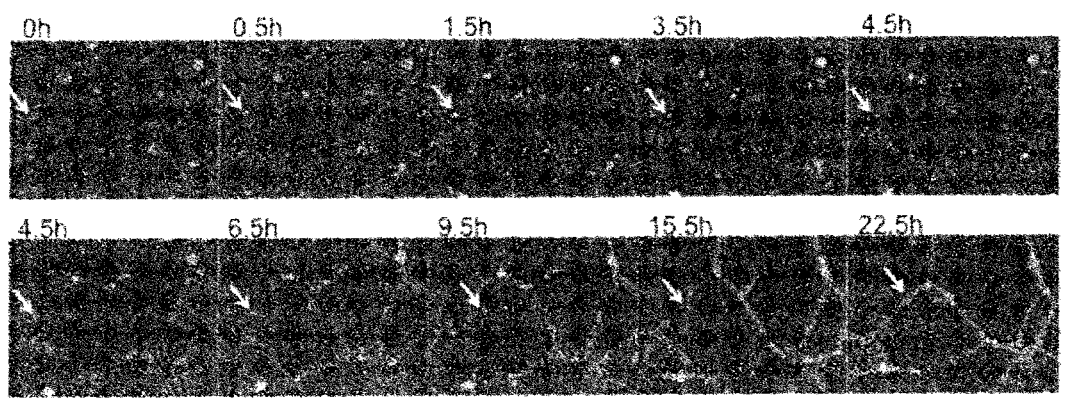
FIG. 9 shows snapshots of life cell imaging of tube formation by endothelial cells and co-localization of pericyte progenitors (life green fluorescent) (24 h, 10× magnification), white arrow follows one single pericyte progenitor.

Endothelial cells form a tubular network on matrigel. When pericyte progenitors were seeded together with endothelial cells they co-localized with forming tubes. Pericyte progenitors alone were not capable of tube formation (FIG. 7). They were sparsely distributed along the tubes and accumulated at sprouting points. Interestingly they did not incorporate into the endothelium but rather attached on top of the tubules (FIG. 8). Life cell imaging of the tube formation by endothelial cells and the co-localization by pericyte progenitors allowed the observation of the process. Pericyte progenitors co-localized with forming tubes at an early stage. Once co-localized they moved along the tubular network (FIG. 9, white arrow). They accumulated at junction points but changed their location and moved to various sprouting points during the time frame taken (white arrow) (FIG. 9).

Figure 10A:
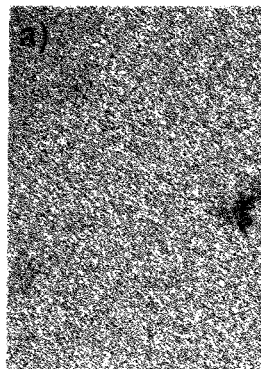
FIGS. 10a and 10b show tube formation assay: 10a) Co-culture of endothelial cells with mesenchymal stem cells (MSC) (10× magnification) and 10b) with macrophages (life green fluorescent labeling) (4× magnification) on matrigel. In contrast to pericyte precursors MSC do not allow any tube formation, as only cell aggregates are visible on matrigel. Macrophages do not inhibit tube formation however, no co-localization with the tubular network can be observed.
Figure 10B:
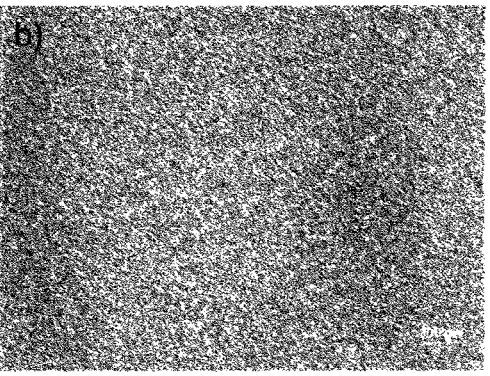

The homing potential to forming tubes and co-localization with tubes and sprouting points is a specific property of pericyte progenitors. Other cell types like mesenchymal stem cells (MSC) did not allow any tube formation, as only cell aggregates were observed in co-culture of MSC and endothelial cells on matrigel (FIG. 10a). In addition other monocyte-derived cells like M-CSF induced macrophages also did not have the ability to co-localize with formed tubes, even if they did not inhibit tube formation like MSC (FIG. 10b).

Pericyte Progenitors Contribute to Endothelial Sprouting

Figure 11:
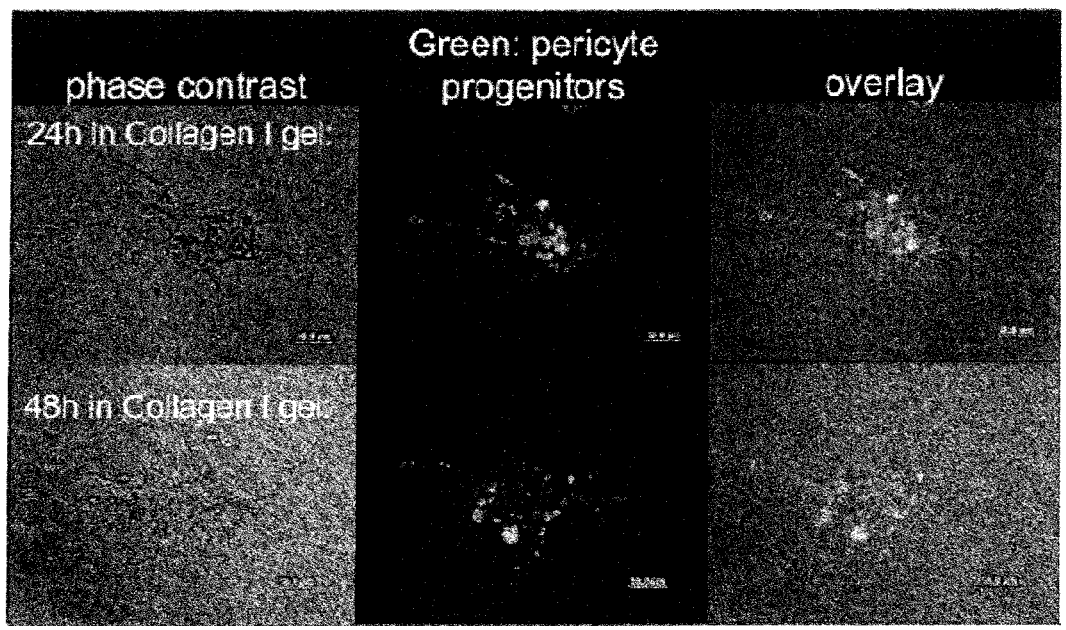
FIG. 11 shows pericyte progenitors (green fluorescent) incorporate into endothelial spheroids and move along newly formed sprouts.

When EC are seeded on non-adherent plates or in hanging drop culture they form cell spheroids. These cell spheroids can be then seeded into collagen I gels, where the cells will bud and form endothelial sprouts into the gel. When generated and green fluorescent-labeled pericyte progenitors were seeded together with endothelial cells, they incorporated into the formed spheroids (FIG. 11). During the course of sprouting in the collagen I gel, they moved from the inner core of the spheroid and along the endothelial sprouts.

Figures 12A, 12B:
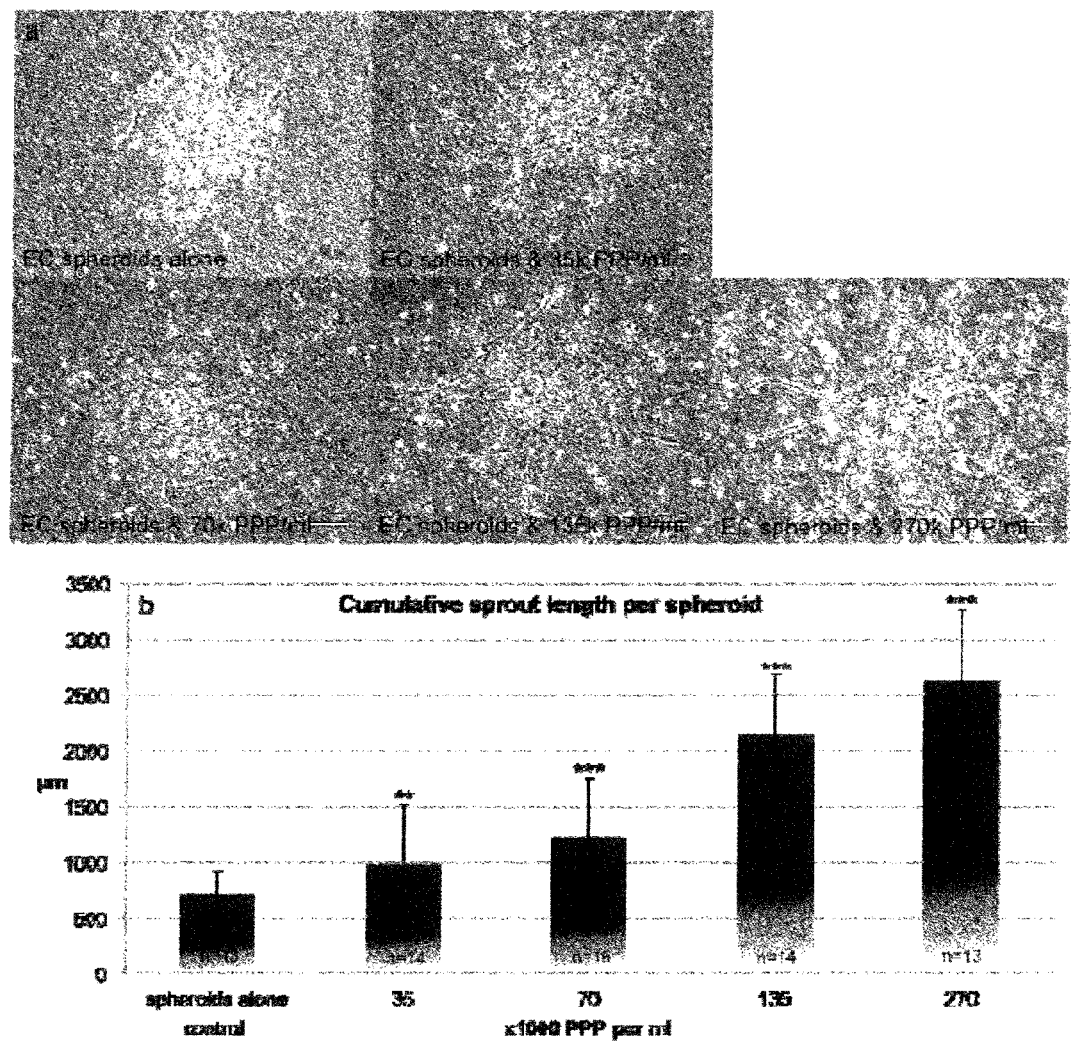
FIGS. 12a and 12b show pericyte progenitors enhance endothelial sprouting (12a and 12b); p<0.01*p<0.00001 as compared to spheroids alone.

The incorporation of generated pericyte progenitors led to the formation of endothelial spheroids of different sizes (FIG. 12). As sprout number and length depends on number of endothelial cells and therefore on spheroid size, the cumulative sprout length per spheroid could not be compared between spheroids of different sizes. To be able to quantify and compare the extent of endothelial sprouting, pericyte progenitors were seeded as a cell suspension into the gel together with spheroids, which only contained EC. Interestingly, even pericyte progenitors not attached, but in close proximity, were able to enhance endothelial sprouting in a dose-dependent manner. In addition, cell debris, which appeared in the core and around the core of the spheroid were only observed in control conditions, where pericyte progenitors were not present. The quality of forming sprouts was also increased in conditions of co-culture with pericyte progenitors. In control conditions sprouts were often disrupted and were an alignment of single cells, which were still defined and could be distinguished from their bordering neighbors. Whereas sprouts formed in co-culture appeared as long coherent tubes.

Figure 13:
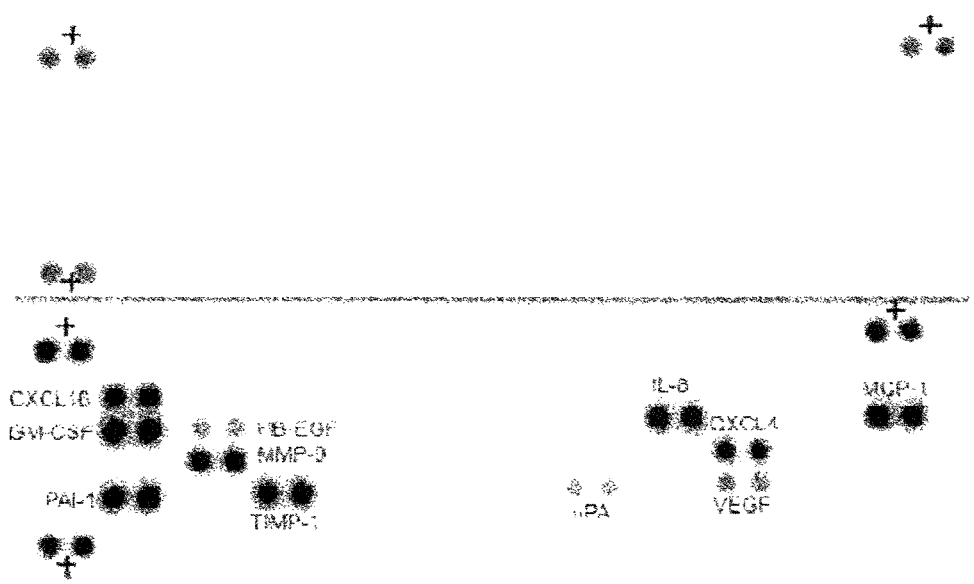
FIG. 13 shows pericyte progenitors express many pro-angiogenic factors. Blank culture media or conditioned by pericyte progenitors was analyzed for the secretion of pro- and anti-angiogenic factors with a proteome array from R&D. The membrane showed the lack of anti-angiogenic but showed a strong signal for pro-angiogenic factors.
Figure 14:
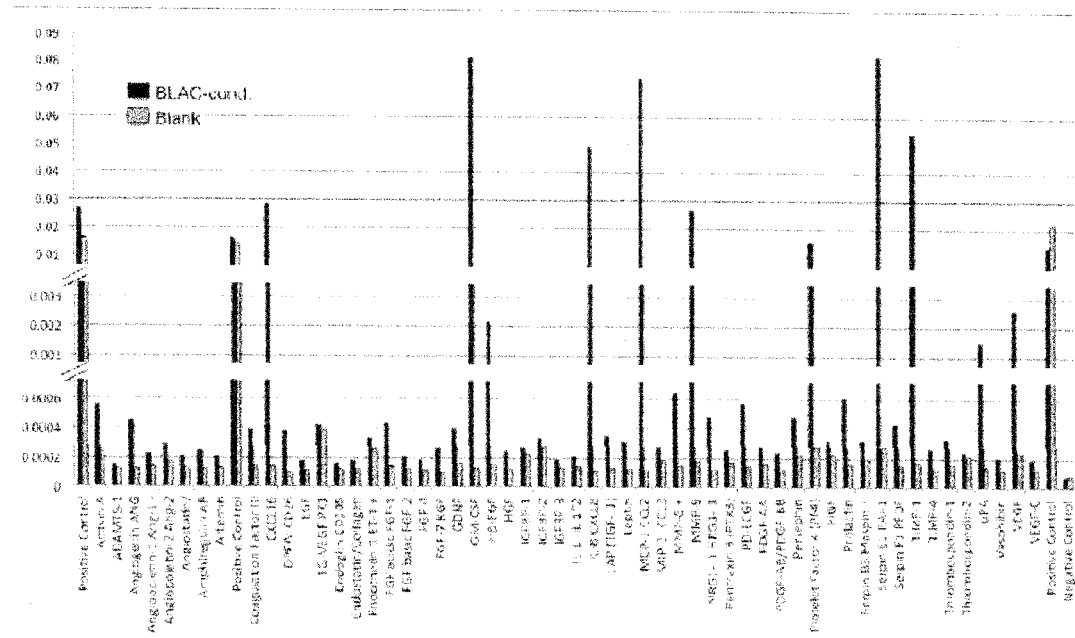
FIG. 14 shows relative quantification of proteome array membrane from R&D. The intensity of stained marker dots was measured using ImageJ and the inverted value of intensity (corresponding the density) was plotted for blank control media or media conditioned by pericyte progenitors.

Pericyte progenitors were analyzed for the expression of anti-angiogenic and pro-angiogenic factors by a proteome array from R&D (FIGS. 13 and 14). It was demonstrated that they lacked expression of the most common anti-angiogenic factors like activin A, high levels of transforming growth factor β-1 (TGFβ-1) (LAP) and interleukin-1 (IL-1) and throbospondin. On the other hand, they expressed proangiogenic factors granulocyte-macrophage colony-stimulating factor (GM-CSF), vascular endothelial growth factor (VEGF) and interleukin-8 (IL-8), which are involved in the stimulation of migration and proliferation of EC and therefore are factors involved in endothelial sprouting. The secretion of proteases and their regulators matrix metalloproteinase 9 (MMP9) and tissue inhibitor of metalloproteinases 1 (TIMP1) as well as urokinase-type plasminogen activator (uPA) and plasminogen activator inhibitor 1 (PAI-1) indicated that pericyte progenitors not only stimulate EC but also actively take part in the sprouting process by digesting extracellular matrix and thereby opening the passages for forming sprouts. Pericyte progenitors also expressed CXCL16, which was shown to also act proangiogenically by enhancing endothelial motility and stabilizing forming tubes in vitro, and heparin-binding epidermal growth factor-like growth factor (HB-EGF) a potent promoter of angiogenesis. Monocyte chemoattractant protein-1 (MCP-1) is a chemokine protein, which attracts progenitor cells to a wound healing sites.

Discussion

The isolation, culture and expansion, and therefore the application in clinics of pericyte progenitors were hindered by the lack of knowledge of their exact origin (e.g., hematopoietic or mesenchymal). Only mature pericytes could be isolated from strongly vascularized tissues. Using a biotechnological cell culture platform, which includes macromolecular crowders in the culture medium, the origin of one pericyte progenitors population was unraveled as hematopoietic and more specifically monocytic, confirming former observations in vivo (Rajantje et al. 2004 Blood, 104(7):2084-2086; Ozerdem et al. 2005 Invest Ophthalmol Vis Sci, 46(10):3502-3506; Song et al. 2009 Cancer Res, 69(15):6057-6064). Generated cells could be identified as pericyte progenitors by expression of early pericyte cell markers (PDGFR-β and NG2). In addition they were distinguishable from other blood-derived progenitors (fibrocyte, MOMC, activated macrophage, endothelial cells) (Bucala et al., 1994 Mol Med, 1(1):71-81; Kuwana et al., 2003 J Leuc Biol, 74(5):833-845; Zhao et al. 2003 Proc Natl Acad Sci, USA, 100(5):2426-2431) by their lack of expression of markers specific for this/these type(s) of cells, namely HLA-DR and collagen I and vWF and CD144.

Further functional assays confirmed their unique pericytic nature, as generated pericyte progenitors not only co-localized with forming capillary networks formed by endothelial cells, but were able to identify and migrate to sprouting points, thereby moving along formed tubular structures. In addition pericyte progenitors were able to contribute to endothelial sprouting and enhance it in a dose-specific manner. They were shown to secrete mainly pro-angiogenic factors, which either influenced endothelial cell sprouting or directly contributed to the sprouting process.

Pericyte progenitors play an important role in tube formation and stabilization and they home to forming tubes in vivo. As shown herein, pericyte progenitors can be generated in a short period of time in clinical relevant numbers. Pericyte progenitors can be used to treat ischemic injuries like stroke, myocardial infarction congestive heart failure and perivascular disorders. In addition they home to revascularizing tissues, like tumors and therefore can be used for cancer detection or as drug delivery vehicles.

The compositions and methods described herein provide for using peripheral blood to generate progenitor cells for revascularisation strategies, this is an elegant, minimally invasive procedure with low risk and from a renewable source. Moreover, the methods use macromolecular crowding in time windows to drive up the pericyte progenitor cell count manifold.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of obtaining pericyte progenitor cells comprising:
   a) culturing blood cells with a matrix to which cells can attach, and one or more carbohydrate-based hydrophilic macromolecules, each of the one or more of the macromolecules has a molecular weight from about 50 kDa to about 1000 kDa, and wherein the one or more macromolecules are present at a concentration from about 2.5 mg/ml to about 100 mg/ml, thereby producing a cell culture; and
   b) maintaining the cell culture under conditions in which pericyte progenitor cells are generated in the cell culture, wherein the pericyte progenitor cells express platelet-derived growth factor receptor-β (PDGFR-β) and neuron-glial antigen 2 (NG2),
   c) thereby obtaining pericyte progenitor cells.

2. The method of claim 1 wherein the blood cells are peripheral blood mononuclear cells (PBMCs).

3. The method of claim 2 wherein about 100,000 pericyte progenitor cell per 1 ml of blood is obtained.

4. The method of claim 1 wherein the matrix comprises all or a portion of an extracellular matrix.

5. The method of claim 4 wherein the matrix comprises fibronectin.

6. The method of claim 1 wherein the culture containing the carbohydrate-based hydrophilic macromolecule has a viscosity of less than about 2 mPas.

7. The method of claim 1 wherein the carbohydrate-based hydrophilic macromolecule has a radius of about 2 to about 50 nm.

8. The method of claim 1 wherein the carbohydrate-based hydrophilic macromolecule is a polymer of glucose, sucrose or a combination thereof.

9. The method of claim 8 wherein the polymer is Ficoll™70, Ficoll™400, polyvinyl pyrrolidone (PVP), dextran, dextran sulfate, polystyrene sulfonate, pullulan, chondroitan sulfate, heparin, heparan sulfate, dermatan sulfate or a combination thereof.

10. The method of claim 1 wherein the blood cells are contacted with a mixture of carbohydrate-based hydrophilic macromolecules comprising Ficoll™70 and Ficoll™400.

11. The method of claim 10 wherein the Ficoll™70 is at a concentration range of from about 7.5 mg/ml to about 100 mg/ml, and the Ficoll™400 is at a concentration range of from about 2.5 mg/ml to about 100 mg/ml.

12. The method of claim 11 wherein the Ficoll™70 is at a concentration of about 37.5 mg/ml and the Ficoll™400 is at a concentration of about 25 mg/ml.

13. The method of claim 1 further comprising detecting pericyte progenitor cells in the cell culture.

14. The method of claim 13 wherein the detection further comprises detecting cells which adhere to the matrix and express platelet-derived growth factor receptor β (PDGFR-β), neuron-glial antigen 2 (NG2), Tie-2, vascular endothelial growth factor receptor-1 (VEGFR-1), VEGFR-2, CD206 or a combination thereof.

15. The method of claim 13 wherein the detection further comprises detecting cells which do not express human leukocyte antigen-DR (HLA-DR), collagen I or a combination thereof.

16. The method of claim 1 wherein the blood cells are contacted with the matrix and one or more carbohydrate-based hydrophilic macromolecules at a seeding concentration of about 10,000 cells/cm$^2$ to about 1,000,000 cells/cm$^2$.

17. The method of claim 1 wherein the conditions under which the cell culture is maintained comprise maintaining the cell culture at about 37° C. in an atmosphere of about 5% $CO_2$/95% air.

18. The method of claim 17 wherein the conditions are maintained for about 1 day to about 14 days.

19. The method of claim 1 wherein the blood cells are human cells.

20. The method of claim 1 further comprising isolating the pericyte progenitor cells from the cell culture.

21. The method of claim 20 wherein the pericyte progenitor cells are isolated by harvesting cells which adhere to the matrix and express platelet-derived growth factor receptor β (PDGFRβ), neuron-glial antigen 2 (NG2), Tie-2, vascular endothelial growth factor receptor-1 (VEGFR-1), VEGFR-2, CD206 or a combination thereof.

* * * * *